United States Patent [19]
Fujishima et al.

[11] Patent Number: 5,851,990
[45] Date of Patent: Dec. 22, 1998

[54] BFGF MUTEIN AND ITS PRODUCTION

[75] Inventors: Akira Fujishima, Sanda; Tsunehiko Fukuda, Kyoto, both of Japan

[73] Assignee: Takeda Chemical Industries, Ltd., Osaka, Japan

[21] Appl. No.: 231,894

[22] Filed: Apr. 22, 1994

Related U.S. Application Data

[63] Continuation of Ser. No. 873,907, Apr. 24, 1992, abandoned.

[30] Foreign Application Priority Data

Apr. 26, 1991 [JP] Japan ..................................... 3-097655
Mar. 24, 1992 [JP] Japan ..................................... 4-066381

[51] Int. Cl.$^6$ ........................... C12N 15/18; A61K 38/18; C07K 14/50
[52] U.S. Cl. ........................... 514/12; 530/399; 536/23.5; 435/69.4; 435/240.2; 435/252.3; 435/320.1
[58] Field of Search ........................... 530/399; 536/23.5; 435/69.4, 69.1; 514/2, 12

[56] References Cited

U.S. PATENT DOCUMENTS

| | | |
|---|---|---|
| 4,518,584 | 5/1985 | Mark et al. ............................. 424/85 |
| 4,588,585 | 5/1986 | Mark et al. ............................. 424/85 |
| 4,853,871 | 8/1989 | Pantoliano et al. .................... 364/496 |
| 4,959,314 | 9/1990 | Mark et al. ............................ 435/69.1 |
| 5,130,418 | 7/1992 | Thompson .............................. 530/399 |
| 5,155,214 | 10/1992 | Baird et al. ............................ 530/399 |

FOREIGN PATENT DOCUMENTS

| | | |
|---|---|---|
| 237966 | 12/1987 | European Pat. Off. . |
| 281822 | 9/1988 | European Pat. Off. . |
| 320148 | 1/1989 | European Pat. Off. . |
| 298723 | 11/1989 | European Pat. Off. . |
| WO89/04832 | 6/1989 | WIPO . |
| WO90/02800 | 3/1990 | WIPO . |
| WO90/13310 | 11/1990 | WIPO . |

OTHER PUBLICATIONS

Abraham et al. *EMBO J.* 5(10):2523–28 (1986).
Zhu et al., Science, 251:90–93, 1991.
Zhang et al., *PNAS* :3446–3450, 1991.

*Primary Examiner*—Marianne P. Allen
*Attorney, Agent, or Firm*—David G. Conlin; David S. Resnick; Dike, Bronstein, Roberts & Cushman, LLP

[57] ABSTRACT

A mutein resulting from substitution of cysteins for at least one of the constitutional amino acids has a high stability, and can serve well as a pharmaceutical, such as a healing promoting agent for wounds.

13 Claims, 19 Drawing Sheets

```
  1
     ProAlaLeuProGluAspGlyGlySerGlyAlaPheProProGlyHisPheLysAsp     19
     ATGCCAGCATTGCCCGAGGATGGCGGCAGCGGGGCCTTCCCCGGCCACTTCAAGGAC
 20
     ProLysArgLeuTyrCysLysAsnGlyGlyPhePheArgIleHisProAspGlyArg     39
     CCCAAGCGGCTGTACTGCAAAAACGGGGGCTTCTTCCGCATCCACCCCGACGGCCGA
 40
     ValAspGlyValArgGluLysSerAspProHisIleLysLeuGlnLeuGlnAlaGluGlu   59
     GTTGACGGGGTCCGGGAGAAGAGCGACCCTCACATCAAGCTACAACTTCAAGCAGAAGAG
 60
     ArgGlyValValSerIleLysGlyValCysAlaAsnArgTyrLeuAlaMetLysGluAsp   79
     AGAGGAGTTGTGTCTATCAAAGGAGTGTGCTAACCGTTACCTGGCTATGAAGGAAGAT
 80
     GlyArgLeuLeuAlaSerLysCysValThrAspGluCysPhePhePheGluArgLeuGlu   99
     GGAAGATTACTGGCTTCTAAATGTGTTACGGATGAGTGTTTCTTTTTTGAACGATTGGAA
100
     SerAsnAsnTyrAsnThrTyrArgSerArgLysTyrThrSerTrpTyrValAlaLeuLys  119
     TCTAATAACTACAATACTTACCGGTCAAGGAAATACACCAGTTGGTATGTGGCACTGAAA
120
     ArgThrGlyLeuGlyTyrLysLeuGlyProGlyGlnLysAlaIleLeuPhe           139
     CGAACTGGGCAGTATAAACTTGGATCCAAAACAGGACCTGGCAGAAAGCTATACTTTTT
140
     LeuProMetSerAlaLysSertrm
     CTTCCAATGTCTGCTAAGAGCTGA
```

FIG. 1

FIG.2(a)
```
                 EcoRI    M   P   A
    5' - G ATT ACG AAT TCT ATG CCA GCA T - 3'
                                  CA
    3' - C TAA TGC TTA GTA TAC GGT CGT - 5'
                     NdeI
```

FIG.2(b)
```
                           118
         S   W   Y   V   A   L   K   R   T   G
    5' - AGT TGG TAT GTG GCA CTG AAA CGA ACT GGG - 3'
                         TGC
    3' - C ATA CAC CGT ACG TTT GCT TGA C - 5'
                         SphI
```

FIG.2(c)
```
                      139
         K   A   I   L   F   L   P   M   S   A
    5' - AAA GCA ATA CTT TTT CTT CCA ATG TCT GCT - 3'
                             G
    3' - CGA TAT GAA ACA GAA GGT TAC - 5'
```

FIG.2(d)
```
                      75
         A   N   R   Y   L   A   M   K   E   D
    5' - GCT AAT CGT TAC CTG GCT ATG AAG GAA GAT GG - 3'
                                 TG
    3' - A GCA ATG GAC ACA TAC TTC CTT - 5'
```

FIG.2(e)
```
                          85
         G   R   L   L   A   S   K   S   V   T   D
    5' - GGA AGA TTA CTA GCT TCT AAG TCT GTT ACG GAT - 3'
                         A  GC
    3' - TCT AAT GAT CGT ACG TTC AGA CAA - 5'
                             SphI
```

```
  1
  ProAlaLeuProGluAspGlyGlySerGlyAlaPheProProGlyHisPheLysAsp     19
  ATGCCAGCATTGCCCGAGGATGGGGGCAGCGGGGCCTTCCCGCCCGGCCACTTCAAGGAC
 20
  ProLysArgLeuTyrCysLysAsnGlyGlyPhePheLeuArgIleHisProAspGlyArg  39
  CCCAAGCGGCTGTACTGCAAAAACGGGGGCTTCTTCCTGCGCATCCACCCCGACGGCCGA
 40
  ValAspGlyValArgGluLysSerAspProHisIleLysLeuGlnLeuAlaGluGlu     59
  GTTGACGGGGTCCGGGAGAAGAGCGACCCTCACATCAAGCTACAACTTCAAGCAGAAGAG
 60
  ArgGlyValValSerIleLysGlyValSerAlaAsnArgTyrLeuAlaMetLysGluAsp  79
  AGAGGAGTTGTGTCTATCAAAGGAGTGAGCGCTAATCGTTACCTGGCTATGAAGGAAGAT
 80
  GlyArgLeuLeuAlaSerLysSerValThrAspGluCysPhePheGluArgLeuGlu     99
  GGAAGATTACTAGCTTCTAAGTCTGTTACGGATGAGTGTTTCTTTTGAACGATTGGAA
100
  SerAsnAsnTyrAsnThrTyrArgSerArgLysTyrThrSerTrpTyrValAlaCysLys 119
  TCTAATAACTACAATACTTACCGGTCAAGGAAATACACCAGTTGGTATGTGGCATGCAAA
120
  ArgThrGlyLeuGlnTyrLysLeuGlyProGlySerLysThrGlyProGlyGlnLysAlaIleLeuPhe 139
  CGAACTGGGCAGTATAAACTTGGATCCAAAAACAGGACCTGGGCAGAAAAGCTATACTTTT
140
  LeuProMetSerAlaLysSerTrm
  CTTCCAATGTCTGCTAAGAGCTGA
```

FIG. 7

```
  1
ProAlaLeuProGluAspGlyGlySerGlyAlaPheProProGlyHisPheLysAsp                    19
ATGCCAGCATTGCCCGAGGATGGCGGCAGCGGGGCCTTCCCCCCGGGCCACTTCAAGGAC
 20
ProLysArgLeuTyrCysLysAsnGlyGlyPhePheLeuArgIleHisProAspGlyArg                 39
CCCAAGCGGCTGTACTGCAAAAACGGGGGCTTCTTCCTGCGCATCCACCCCGACGGCCGA
 40
ValAspGlyValArgGluLysSerAspProHisIleLysLeuGlnLeuGlnAlaGluGlu                 59
GTTGACGGGGTCCGGGAGAAGAGCGACCCCCACATCAAGCTACAACTTCAAGCAGAAGAG
 60
ArgGlyValValSerIleLysGlyValSerAlaAsnArgTyrLeuAlaMetLysGluAsp                 79
AGAGGAGTTGTGTCTATCAAAGGAGTGAGCGCTAATCGTTACCTGGCTATGAAGGAAGAT
 80
GlyArgLeuLeuAlaSerLysSerValThrAspGluCysPhePheGluArgLeuGlu                    99
GGAAGATTACTAGCTTCTAAGTCTGTTACGGATGAGTGTTTCTTTTTGAACGATTGGAA
100
SerAsnAsnTyrAsnThrTyrArgSerArgLysTyrThrSerTrpTyrValAlaLeuLys                119
TCTAATAACTACAATACATACCGGTCAAGGAAATACACCAGTTGGTATGTGGCACTGAAA
120
ArgThrGlyGlnTyrLysLeuLeuGlySerLysThrGlyProGlyLysAlaIleLeuCys                139
CGAACTGGGCAGTATAAACTTGGATCCAAAACAGGACCTGGGAAAGCTATACTTTGT
140
LeuProMetSerAlaLysSertrm
CTTCCAATGTCTGCTAAGAGCTGA
```

FIG. 10

```
  1
  ProAlaLeuProGluAspGlyGlySerGlyAlaPheProProGlyHisPheLysAsp    19
ATGCCAGCATTGCCCGAGGATGGTGGCAGCGGCGGCCCTTCCCGCCGGCCACTTCAAGGAC
 20
  ProLysArgLeuTyrCysLysLysAsnGlyGlyPheLeuArgIleHisProAspGlyArg  39
CCCAAGCGGCTGTACTGCAAAAAACGGGGGCTTCTTCCTGCGCATCCACCCCGACGGCCGA
 40
  ValAspGlyValArgGluLysSerAspProHisIleLysLeuGlnLeuGlnAlaGluGlu  59
GTTGACGGGGTCCGGGAGAAGAGCGACCCTCACATCAAGCTACAACTTCAAGCAGAAGAG
 60
  ArgGlyValValSerIleLysGlyValSer AlaAsnArgTyrLeuCysMetLysGluAsp 79
AGAGGAGTTGTGTCTATCAAAGGAGTGAGCGCTAATCGTTACCTGTGTATGAAGGAAGAT
 80
  GlyArgLeuLeuAlaSerLysSer ValThrAspGluCysPhePheGluArgLeuGlu    99
GGAAGATTACTAGCTTCTAAGTCTGTTACGGATGAGTGTTTCTTTTTGAACGATTGGAA
100
  SerAsnAsnTyrAsnThrTyrArgSerArgLysTyrThrSerTrpTyrValAlaLeuLys  119
TCTAATAACTACAATACTTACCGGTCAAGGAAATACACCAGTTGGTATGTGGCACTGAAA
120
  ArgThrGlyGlnTyrLysLeuGlyProGlyGlnLysAlaIleLeuPhe              139
CGAACTGGGCAGTATAAACTTGGATCCAAAACAGGACCTGGGCAGAAAGCTATACTTTTT
140
  LeuProMetSerAlaLysSertrm
CTTCCAATGTCTGCTAAGAGCTGA
```

FIG. 13

```
      1
      ProAlaLeuProGluAspGlySerGlyAlaPheProProGlyHisPheLysAsp         19
ATGCCAGCATTGCCCGAGGATGGCGGCAGCGGGGCGCCCTTCCCGCCCGGCCACTTCAAGGAC
     20
     ProLysArgLeuTyrCysLysLysAsnGlyGlyPhePheLeuArgIleHisProAspGlyArg 39
CCCAAGCGGCTGTACTGCAAAAACGGGGGCTTCTTCCTGCGCATCCACCCCGACGGCCGA
     40
     ValAspGlyValArgGluLysSerAspProHisIleLysLeuGlnLeuAlaGluGlu       59
GTTGACGGGGTCCGGGAGAAGAGCGACCCTCACATCAAGCTACAACTTCAAGCAGAAGAG
     60
     ArgGlyValValSerIleLysGlyValSer AlaAsnArgTyrLeuAlaMetLysGluAsp   79
AGAGGAGTTGTGTCTATCAAAGGAGTGAGCGCTAATCGTTACCTGGCTATGAAGGAAGAT
     80
     GlyArgLeuLeuAlaCysLysSer ValThrAspGluCysPhePheGluArgLeuGlu      99
GGAAGATTACTAGCATGCAAGTCTGTTACGGATGAGTGTTTCTTTTTGAACGATTGGAA
     100
     SerAsnAsnTyrAsnThrTyrArgSerArgLysTyrThrSerTrpTyrValAlaLeuLys    119
TCTAATAACTACAATACTTACCGGTCAAGGAAATACACCAGTTGGTATGTGGCACTGAAA
     120
     ArgThrGlyGlnTyrLysLeuGlySerLysThrGlyProGlyGlnLysAlaIleLeuPhe    139
CGAACTGGGCAGTATAAACTTGGATCCAAAACAGGACCTGGGCAGAAAGCTATACTTTT
     140
     LeuProMetSerAlaLysSertrm
CTTCCAATGTCTGCTAAGAGCTGA
```

FIG. 16

Retention time (minutes)

BFGF MUTEIN AND ITS PRODUCTION

This application is a continuation of Ser. No. 873,907 filed Apr. 24, 1992, now abandoned.

FIELD OF THE INVENTION

The present invention relates to a mutein of basic fibroblast growth factor (hereinafter also referred to as bFGF for short) and a method of its production.

BACKGROUND OF THE INVENTION bFGF, a basic polypeptide with a molecular weight of about 17000 was first isolated as a factor possessing strong growth promoting action on fibroblasts such as BALB/c3T3 cells [D. Gospodarowicz, Nature, 249, 123 (1974)]. It was then found to possess growth promoting action on almost all types of mesophile-derived cells [D. Gospodarowicz et al., National Cancer Institute Monograph, 48, 109 (1978)]. Particularly, the angiogenic action of bFGF, along with its cell growth promoting action, suggest potential for its use as a therapeutic drug for the treatment of injuries and as a preventive and therapeutic drug for the treatment of thrombosis, arteriosclerosis and other diseases.

Bovine bFGF was first reported in the Proceedings of the National Academy of Science of the United States, 82, 6507–6511 (1985). The amino acid composition of bovine bFGF, estimated from a cloned cDNA thereof, is shown in Science, 233, 545 (1986).

As for human bFGF, its extraction from the human brain is reported in Biochemical and Biophysical Research Communications, 135, 541 (1986).

Also, EMBO Journal (European Molecular Biology Organization Journal), 5, 2523 (1986) and PCT International Patent Publication No. WO87/01728 show the amino acid composition of human bFGF estimated from a clone obtained by cloning a cDNA of human bFGF using bovine bFGF as a probe.

Production of human bFGF by cloning a cDNA of human bFGF and cultivating the transformant is described in FEBS Letters, 213, 189 (1987) and Biochemical and Biophysical Research Communications, 146, 470–477 (1987). (The base sequence of the cDNA used and the amino acid sequence of human bFGF are shown in FIG. 1.)

SUMMARY OF THE INVENTION

The present inventors expected that modification of the amino acid sequence of bFGF would increase the stability, cellular productivity and cell growth promoting activity of the molecule and provide potentially useful unknown bioactivities.

On a note related to stability, protein denaturation is often accompanied by a loss of bioactivity. Stability of the higher structure of protein is therefore a key point when the protein is used as a pharmaceutical. The higher structure of a protein is considered to depend basically on the primary structure; its stability is attributed mainly to the interaction of amino acid side chains or between side chains and the polypeptide main chain, i.e., hydrogen bonds, S—S bonds of cysteine residues, electrostatic attracting force and hydrophobic bonds.

bFGF contains four Cys residues, but they are not essential to the activity of bFGF, none forming an intramolecular S—S bond [X. Zhu et al., Science, 251, 90–93 (1991)]. This means that the higher structure of bFGF is based on the above-mentioned hydrogen bonds, electrostatic attracting force, hydrophobic bonds etc., and is not subject to strong constraint of covalent bonds (S—S bonds). This results in a high degree of freedom of intramolecular movement of bFGF, thus largely accounting for the fact that this protein is apt to denature under various sets of physical and chemical conditions.

Seno et al. (Japanese Patent Application Laid-open No. 1-93/1990 which corresponds to EP-A-281,822) attempted to obtain a stabler bFGF mutein by substituting amino acids constituting the bFGF molecule and various other amino acids. They achieved remarkable success in stabilizing the molecule, hence improving bFGF purification efficiency by substituting residues of Ser and other amino acids for Cys residues to reduce or eliminate the probability of existing Cys residues forming an intermolecular or undesirable intramolecular S—S bond.

The present inventors provided the security and stabilization of the higher structure of bFGF by preparing a mutein wherein constitutional amino acids of bFGF are replaced by other amino acids, particularly cysteine, and causing these newly introduced cysteine residues to form previously non-existent S—S bonds, either among themselves or with cysteine residues originally present in the bFGF molecule.

When an S—S bond is newly formed in a protein molecule, the side chains of the cysteine residues involved should be spatially close to each other. For this reason, information on higher structure obtained by X-ray crystallographic analysis is very useful, making logical and efficient research possible in obtaining a protein of the desired nature. The inventors succeeded in crystallizing bFGF and a mutein thereof (Japanese Patent Application Laid-open No. 47198/1991) and analyzed their steric structures H. Ago et al. J. Biochem. 110, 360–363 (1991).

On the basis of the findings from this work, the inventors prepared a modified bFGF mutein by recombinant DNA technology and site-directed mutagenesis, and investigated improvement in stability, increase in cellular productivity and activity and change in bioactivities, and found that improved stability is seen in a mutein resulting from substitution of cysteine for at least one of the constitutional amino acids of bFGF or an active derivative thereof. The inventors made further investigations based on this finding, and thus developed the present invention.

The present invention provides:

(1) a mutein resulting from substitution of cysteine for at least one of the amino acids constituting bFGF or an active derivative thereof, (2) a recombinant DNA having the base sequence which codes for the mutein of (1) above, (3) a vector containing the recombinant DNA of (2) above, (4) a transformant carrying the vector of (3) above, (5) a method of producing the mutein of (1) above characterized by cultivation of the transformant of (4) above in culture medium, (6) a method of producing a mutein wherein an intramolecular disulfide bond (S—S bond) has been formed between two cysteine residues in the molecule of the mutein of (1) above by subjecting the mutein of (1) to an oxidative reaction, (7) a pharmaceutical composition comprising an effective amount of a mutein in accordance with the mutein (1) as an active ingredient in a pharmaceutically acceptable carrier to provide a healing action for the treatment of burns, wounds, postoperative tissue healing, (8) a pharmaceutical composition comprising an effective amount of a mutein in accordance with the mutein (1) as an active ingredient in a pharmaceutically acceptable carrier to provide a therapeutic action on thrombosis and, arteriosclerosis, and (9) a method for producing a pharmaceutical composition of said (7) or (8) by mixing the mutein (1) with a pharmaceutically acceptable carrier.

BRIEF DESCRIPTION OF THE DRAWINGS

FIG. 1 (SEQ ID NO: 6) shows an example of the base sequence which codes for naturally occurring human bFGF and the amino acid sequence (SEQ ID NO: 11) of human bFGF.

FIG. 2a–e show the primers used for site-directed mutagenesis in Examples 1, 2, 3, 4 and 5, together with the sequences of the corresponding portions before mutation (shown in the upper columns).

In FIG. 2, the upper column of (a) shows sequence before mutation and the lower column of (a) shows oligonucleotide 1(SEQ ID NO: 5); the upper column of (b) shows sequence before mutation and the lower column of (b) shows oligonucleotide 2(SEQ ID NO: 1); the upper column of (c) shows sequence before mutation and the lower column of (c) shows oligonucleotide 3(SEQ ID NO: 2); the upper column of (d) shows sequence before mutation and the lower column of (d) shows oligonucleotide 4(SEQ ID NO: 3); and the upper column of (e) shows sequence before mutation and the lower column of (e) shows oligonucleotide 5 (SEQ ID NO: 4).

FIG. 7 (SEQ ID NO: 7) shows the base sequence which codes for the human bFGF mutein BFM2, carried by the plasmid pBFM2 obtained in Example 2, and the corresponding amino acid sequence (SEQ ID NO: 12). Each underline shows a base different from the counterpart in the naturally occurring type; each upper line shows an amino acid residue different from the counterpart in the naturally occurring type.

FIG. 10 (SEQ ID NO: 8) shows the base sequence which codes for the human bFGF mutein BFM3, carried by the plasmid pBFM3 obtained in Example 3, and the corresponding amino acid sequence (SEQ ID NO: 13). Each underline shows a base different from the counterpart in the naturally occurring type; each upper line shows an amino acid residue different from the counterpart in the naturally occurring type.

FIG. 13 (SEQ ID NO: 9) shows the base sequence which codes for the human bFGF mutein BFM4, carried by the plasmid pBFM4 obtained in Example 4, and the corresponding amino acid sequence (SEQ ID NO: 14). Each underline shows a base different from the counterpart in the naturally occurring type; each upper line shows an amino acid residue different from the counterpart in the naturally occurring type.

FIG. 16 (SEQ ID NO: 10) shows the base sequence which codes for the human bFGF mutein BFM5, carried by the plasmid pBFM5 obtained in Example 5, and the corresponding amino acid sequence (SEQ ID NO: 15). Each underline shows a base different from the counterpart in the naturally occurring type; each upper line shows an amino acid residue different from the counterpart in the naturally occurring type.

Lane 1: Molecular weight marker
Lane 2: BFM2, before IPTG addition
Lane 3: BFM2, 3 hours after IPTG addition
Lane 4: BFM3, before IPTG addition
Lane 5: BFM3, 3 hours after IPTG addition
Lane 6: BFM4, before IPTG addition
Lane 7: BFM4, 3 hours after IPTG addition
Lane 8: BFM5, before IPTG addition
Lane 9: BFM5, 3 hours after IPTG addition
Lane 10: Purified mutein CS23

Figures 18A, 18B:
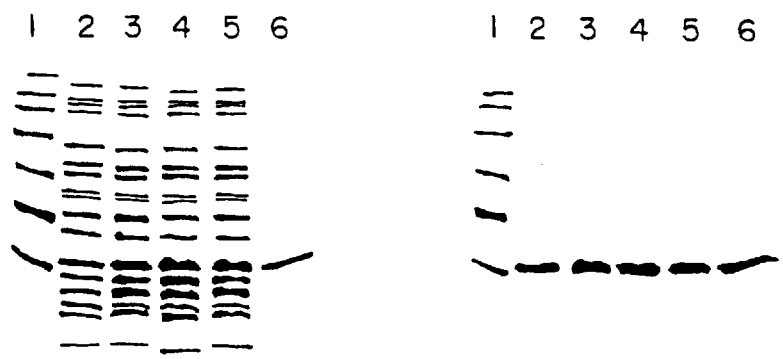

FIGS. 18 A–B show the results of SDS-PAGE and immunoblotting of the cells caused to express the mutein in Examples 2 (2), 3 (2), 4 (2) and 5 (2).

In FIG. 18, "A" represents protein staining with Coomassie Brilliant Blue, "B" immunoblotting; lanes 1 through 5 denote the following:

Lane 1: Molecular weight marker
Lane 2: BFM2
Lane 3: BFM3
Lane 4: BFM4
Lane 5: BFM5
Lane 6: Purified mutein CS23

Figure 19:
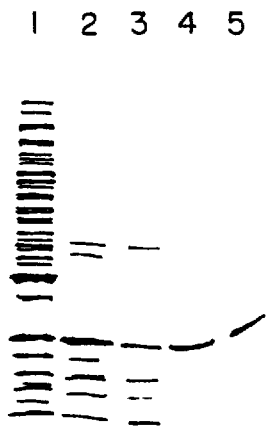

FIG. 19 shows the results of SDS-PAGE of the sample during purification of BFM5 in Example 6.

In FIG. 19, lanes 1 through 5 denote the following:

Lane 1: QAE-Toyopearl column effluent fraction, 4.5 µl
Lane 2: CM-Toyopearl column eluate (2-fold dilution), 10 µl
Lane 3: CM-Toyopearl column eluate (2-fold dilution), 3.5 µl
Lane 4: Purified mutein BFM5, 1.1 µl (1.0 µg)
Lane 5: Purified mutein CS23

Figure 20A:
Figure 20B:

FIG. 20 (A) shows the results of SDS-PAGE, obtained in Example 7, of a BFM4 sample being purified. FIG. 20 (B) shows the results of non-reducing SDS-PAGE, obtained in Example 8, of BFM4 before oxidation (reduced BFM4) and after oxidation (oxidized BFM4).

Figure 21A:
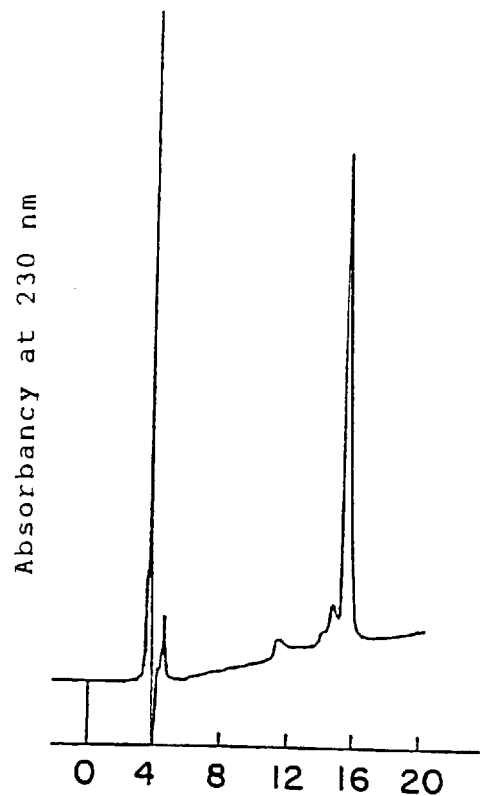
Figure 21B:
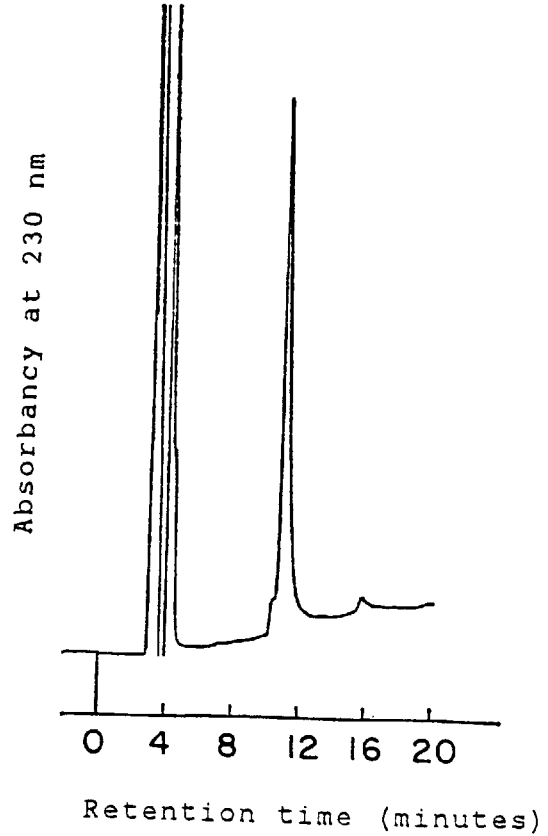

FIG. 21 (A) shows the reverse phase HPLC elution pattern, obtained in Example 8, of BFM4 before oxidation. FIG. 21 (B) shows the reverse phase HPLC elution pattern, obtained in Example 8, of BFM4 after oxidation.

Figure 22:
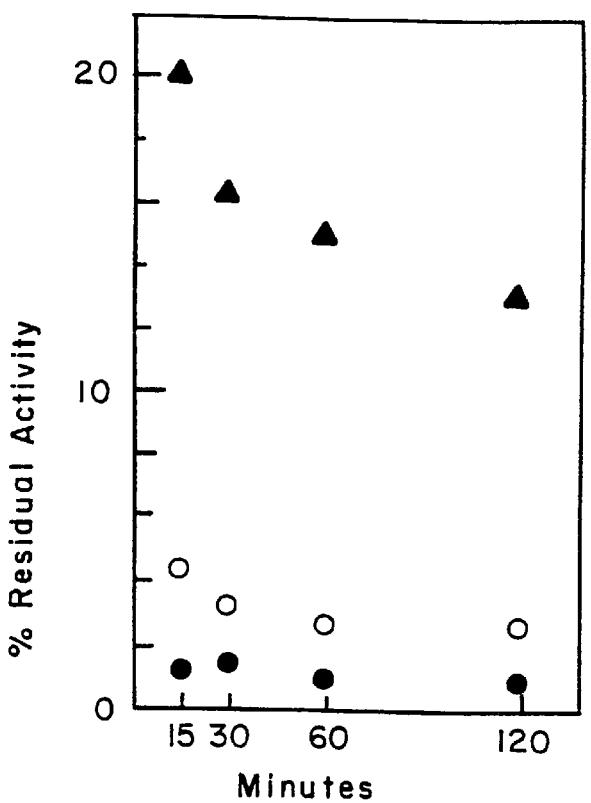

FIG. 22 shows the stability of oxidized BFM4 obtained under conditions of pH 2 and 37° C. in Example 9.

Figure 23:
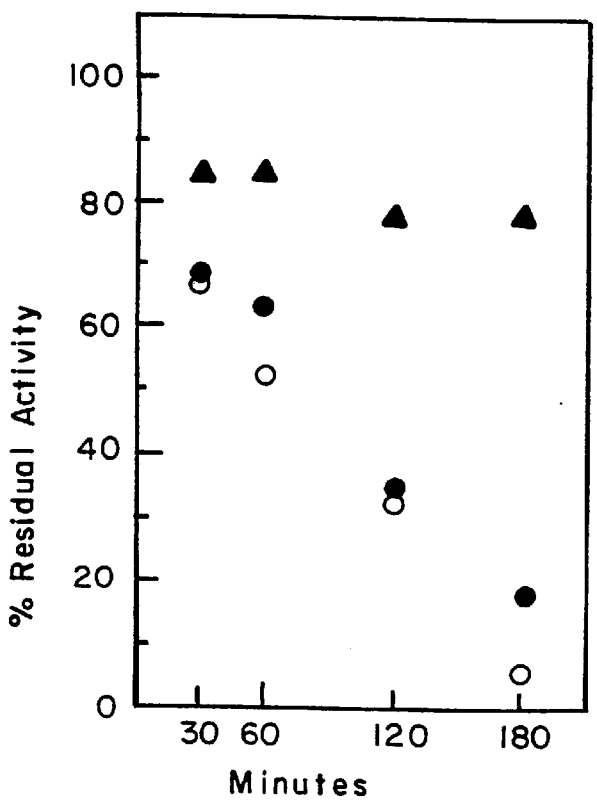

FIG. 23 shows the stability of oxidized BFM4 obtained under conditions of pH 7.4 and 50° C. in Example 10.

DETAILED DESCRIPTION OF THE INVENTION

The present invention provides a mutein resulting from substitution of cysteine for at least one of the amino acids constituting bFGF or an active derivative thereof.

As a preferred embodiment, there is provided a mutein (1-2) wherein a cysteine introduced by substitution is located at a position where the substituted cysteine and a second cysteine form a mutual disulfide bond.

Further, in preferred embodiements of said mutein (1-2), it is preferable that said second cysteine is a constituent amino acid of bFGF. Preferred positions for the second cysteine include the position 25 or 92 of human bFGF or bovine bFGF. When the second cysteine is that at the position 25, the preferred position of the first cysteine is the positions of 118 or 139, and when the second cysteine is that at the position 92, the preferred position of the first cysteine is the positions of 75 or 85.

In certain embodiments of said mutein (1-2), it is preferable that an even number of cysteines are introduced by substitution so that each pair of cysteines are sufficiently spaces so as to form a disulfide bond. The location pairs are exemplified by the positions 20 and 52; 21 and 142; 27 and 135; 33 and 50; 49 and 69; and 81 and 126 of human bFGF or bovine bFGF. Examples of said even numbers include even numbers of 2 through 8 and preferably of 2 through 4. Incidentally, in this case, the muteins in which cysteine (s) introduced by substitution does (do) not form disulfide bond are also included.

Furthermore, the mutein of the present invention preferably has a disulfide bond (hereinafter it is sometimes abbreviated an "S—S bond") formed between two cysteine residues in the molecule thereof.

The bFGF for the present invention may be derived from mammals. Examples of source mammals include humans, monkeys, swine, bovines, sheep and horses. The bFGF may be extracted from various organs which have already been found to contain it, such as the brain and the pituitary. The bFGF may also be obtained by recombinant DNA technology [FEBS Letters, 213, 189–194 (1987); European Patent Publication No. 237,966)].

Examples of active derivatives of bFGF include muteins of bFGF possessing activities similar to those of bFGF.

The bFGF mutein is essentially an amino acid sequence variant of the original peptide or protein. Accordingly, such muteins include amino acid addition, constitutional amino acid deletion and/or replacement by other amino acids.

Examples of the bFGF mutein include the muteins described in Biochemical and Biophysical Research Communications, 151, 701–708 (1988), European Patent Publication (hereinafter also referred to as EP for short) No. 281,822, No. 326,907, No. 394,951, No. 298,728 and PCT WO89/04832.

To produce the mutein of the present invention, site-directed mutagenesis is used in addition to conventional recombinant DNA technology. This technique, known to those skilled in the art, is described by R. F. Lather and J. P. Lecoq in Genetic Engineering, Academic Press (1983), 31-50. Oligonucleotide-directed mutagenesis is described by M. Smith and S. Gillam in Genetic Engineering: Principles and Methods, Plenum Press (1981), 3, 1–32.

To produce the structural gene which codes for the mutein of the present invention, the following steps are followed:

(a) a single-stranded DNA comprising a single chain of the structural gene of bFGF is hybridized to a mutational oligonucleotide primer, (b) the primer is elongated by DNA polymerase to form a mutated heteroduplex, and (c) this mutated heteroduplex is replicated.

The size of the oligonucleotide primer depends on the conditions necessary for stable hybridization of the primer with the gene region in which the mutation in induced, and on the limitations in the currently available method for oligonucleotides synthesis. The factors to be considered in designing the oligonucleotide used for oligonucleotide-directed mutagenesis (e.g., overall size, mutational site detouring portion size) are described by M. Smith and S. Gillam (the same publication as above). Generally, the total length of the oligonucleotide is such that stable and unique hybridization at the mutational site is optimized, and the sizes of the extensions from the mutational site to the 5'- and 3'-terminals are set so as to avoid mutational editing by the exonuclease activity of DNA polymerase. The oligonucleotide used for mutagenesis in accordance with the present invention contains normally about 12 to 24 bases, preferably about 14 to 20 bases, and more preferably about 14 to 18 bases. These normally include at least about 3 of the codons to be changed on the 3'-terminal side.

For example, to obtain a mutein wherein the constitutional amino acid leucine has been replaced by cysteine, a synthetic nucleotide primer which changes the leucine codon to the cysteine codon is used for site-directed mutagenesis to yield a modified bFGF gene. To change a leucine residue of human bFGF (118-position) to cysteine, the primer is hybridized to the sense chain of the FGF gene. Examples of preferred nucleotide primers include 5'-CAGTTCG<u>TTT</u>GCATGCCACATAC-3'(SEQ ID NO: 1) (the underline indicates the changed codon).

Examples of preferred primers for changing phenylalanine (139-position) to cysteine include 5'-CATTGGAAG <u>ACA</u>AAGTATAGC-3'(SEQ ID NO: 2) (the underline indicates the changed codon).

Examples of preferred primers for changing alanine (75-position) to cysteine include 5'-TTCCTTCAT <u>ACA</u>CAGGTAACGA-3'(SEQ ID NO: 3) (the underline indicates the changed codon).

Examples of preferred primers for changing serine (85-position) to cysteine include 5'-AACAGACTT <u>GCA</u>TGCTAGTAATCT-3'(SEQ ID NO: 4) (the underline indicates the changed codon).

The primer is hybridized to a single-stranded phage cloned from a single-stranded chain of the bFGF gene, such as M13 [Yanisch-Perror, C. Vieira and J. Messing, Gene, 33, 103–119 (1985); Messing J., Methods in Enzymology, 101, 20–78 (1983)], fd [R. Herrman et al., Molecular and General Genetics, 177, 231 (1980)] or Φx174 [M. Smith and S. Gillam, Genetic Engineering, Plenum Press, 3, 1–32 (1981) ], or a phage-plasmid chimeric vector such as pUC118 or pUC119 [J. Vieira and J. Messing, Methods in Enzymology, 153, 3–11 (1987)]. The phage is recognized as capable of carrying a chain of the gene irrespective of whether it is a sense or antisense chain. When the phage carries an antisense chain, the primer may, due to codon degeneration, be unidentical with the sense chain region containing the codon to be mutated, in addition to the disagreement with this codon, thus determining a triplet encoding another amino acid. Similarly, when the phage carries a sense chain, the primer may not be complementary to the sense chain region containing the codon to be mutated, except for appropriate disagreements in the triplet pairing with the codon to be deleted. Conditions used for this hybridization are described by M. Smith and S. Gillam (same publication as above). Temperature normally ranges from about 0° C. to 70° C., more commonly from about 10° C. to 50° C. After hybridization, the primer is elongated on the phage DNA by reaction with *Escherichia coli* DNA polymerase I, T4 DNA polymerase, reverse transcriptase or another appropriate DNA polymerase. The resulting dsDNA is converted to cyclic dsDNA by treatment with a DNA ligase such as T4 DNA ligase. DNA molecules having a single-stranded region can be disrupted by S1 endonuclease treatment.

The resulting mutated heteroduplex is used to transform infectable host organisms or cells. In the replication of the heteroduplex in a host, offspring emerge from both chains. Replication is followed by isolation of the mutant gene from the mutant chain offspring, which is then inserted into an appropriate vector, which is used to transform an appropriate host organism or cell.

Next, the phage DNA carrying the mutated gene is isolated and inserted into a plasmid.

Examples of the plasmid for DNA insertion include plasmids derived from *Escherichia coli* such as pBR322 [Gene, 2, 95 (1977)], pBR325 [Gene, 4, 121 (1978], pUC12 [Gene, 19, 259 (1982)] and pUC13 [Gene, 19, 259 (1982)] and those derived from *Bacillus subtilis* such as pUB110 [Biochemical and Biophysical Research Communications, 112, 678 (1983)], but any other can be used for this purpose, as long as it is replicable in the host.

Examples of the method of insertion into the plasmid include that described by T. Maniatis et al. in Molecular Cloning, Cold Spring Harbor Laboratory, page 239 (1982).

The cloned gene is joined to the downstream of the promoter, in a vehicle (vector) suitable for its expression, to yield an expression vector.

Examples of vectors include the above-mentioned plasmids derived from *Escherichia coli* (e.g., pBR322, pBR325, pUC12, pUC13), plasmids derived from *Bacillus subtilis* (e.g., pUB110, pTP5, pC194), yeast-derived plasmids (e.g., pSH19, pSH15), bacteriophages such as λ phage, and animal viruses such as retrovirus and vaccinia virus.

The gene may have ATG as a translational initiation codon at its 5'-terminal and TAA, TGA or TAG as a translational termination codon at its 3'-terminal. To express the gene, a promoter is ligated to its upstream. Any promoter can be used for the present invention, as long as it is appropriate for the host used to express the gene.

Examples of preferred promoters include the trp promoter, lac promoter, rec A promoter, λPL promoter, lpp promoter and phage T7Φ10 promoter when the transformation host is a bacterium of the genus Escherichia; the SPO1 promoter, SPO2 promoter and pen P promoter when the host is a bacterium of the genus Bacillus; and the PH05 promoter, PGK promoter, GAP promoter and ADH promoter when the host is a yeast. Preference is given to the case in which a bacterium of the genus Escherichia is used as host in combination with the trp promoter, λPL promoter or phage T7Φ10 promoter.

When the host is an animal cell, preferable promoters include the SV40-derived promoter and retrovirus promoter, with preference given to the SV40-derived promoter.

The thus-constructed vector, harboring a recombinant DNA having the mutein-encoding base sequence, is used to produce a transformant carrying said vector.

Examples of the host include bacteria of the genus Escherichia, bacteria of the genus Bacillus, yeasts and animal cells.

Examples of the bacteria of the genus Escherichia include *Escherichia coli* K12DH1 [Proceedings of the National Academy of Science, USA, 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], MM294 [Proceedings of the National Academy of Science, USA, 73, 4174 (1976)] and MM294(DE3)/pLysS (Japanese Patent Publication Open to Public Inspection No. 43088/1991).

Examples of the bacteria of the genus Bacillus include *Bacillus subtilis* MI 114 [Gene, 24, 255 (1983)] and 207-21 [Journal of Biochemistry, 95, 87 (1984)].

Examples of the yeasts include *Saccharomyces cerevisiae* AH22R−, NA87-11A and DKD-5D.

Examples of animal cells include simian cells COS-7, Vero, Chinese hamster cells CHO, mouse L cells and human FL cells.

The bacteria of the genus Escherichia can be transformed in accordance with the method described in the Proceedings of the National Academy of Science, USA, 69, 2110 (1972), Gene, 17, 107 (1982) and other publications, for instance.

Bacteria of the genus Bacillus can be transformed in accordance with the method described in Molecular and General Genetics, 168, 111 (1979) and other publications, for instance.

Yeasts can be transformed in accordance with the method described in the Proceedings of the National Academy of Science, USA, 75, 1929 (1978), for instance.

Animal cells can be transformed in accordance with the method described in Virology, 52, 456 (1973), for instance.

A transformant carrying a vector harboring a recombinant DNA having a mutein-encoding base sequence is thus obtained.

The mutein of the present invention is produced by cultivating said transformant in culture medium.

For cultivating a transformant whose host is a bacterium of the genus Escherichia or Bacillus, it is appropriate to use liquid medium supplemented with carbon sources, nitrogen sources, minerals and other substances necessary for the growth of the transformant. Examples of carbon sources include glucose, dextrin, soluble starch and sucrose. Examples of nitrogen sources include organic or inorganic substances such as ammonium salts, nitrates, corn steep liquor, peptone, casein, meat extracts, soybean cake and potato extracts. Examples of minerals include calcium chloride, sodium dihydrogen phosphate and magnesium chloride. Yeasts, vitamins, growth promoters and other additives may be added.

The pH of the medium is preferably about 6 to 8.

Examples of media preferably used to cultivate Escherichia bacteria include the M9 medium containing glucose and casamino acid [Miller, Journal of Experiments in Molecular Genetics, 431–433, Cold Spring Harbor Laboratory, New York (1972)]. To increase promoter efficiency as necessary, a chemical agent such as 3β-indolyl acrylic acid or isopropyl βD-thiogalactopyranoside may be added.

When the host is a bacterium of the genus Escherichia, cultivation is normally carried out at about 15° to 43° C. for about 3 to 24 hours, with aeration and/or stirring as necessary.

When the host is a bacterium of the genus Bacillus, cultivation is normally carried out at about 30° to 40° C. for about 6 to 24 hours, with aeration and/or stirring as necessary.

Examples of media for cultivating a transformant whose host is a yeast include Burkholder's minimal medium

[Bostian, K. L. et al., Proceedings of the National Academy of Science, USA, 77, 4505 (1980)]. It is preferable to adjust the medium to a pH of about 5 to 8. Cultivation is normally carried out at about 20° to 35° C. for about 24 to 72 hours, with aeration and/or stirring as necessary.

Examples of media for cultivating a transformant whose host is an animal cell include AIEM medium containing about 5 to 20% fetal bovine serum [Science, 122, 501 (1952)], DMEM medium [Virology, 8, 396 (1959)], RPMI 1640 medium [Journal of the American Medical Association, 199, 519 (1967)] and 199 medium [Proceedings of the Society for the Biological Medicine, 73, 1 (1950)]. The pH is preferably about 6 to 8. Cultivation is normally carried out at about 30° to 40° C. for about 15 to 60 hours, with aeration and/or stirring as necessary.

Separation and purification of mutein from the culture described above can be achieved by the following method.

First, the cultured bacterial cells, yeasts or animal cells are disrupted to extract their content. For this purpose, a large number of means are available, including French press, ultrasound, lysozyme, freeze-thawing and glass beads, with preference in this case given to a combination of lysozyme and ultrasound. Addition of a reducing agent, such as dithiothreitol, to the buffer before disrupting the bacterial or animal cells can increase recovery of the desired mutein. The concentration of the reducing agent is preferably about 1 mM to 100 mM. However, when using lysozyme, the reducing agent is added after lysozyme reaction.

Next, the cell extract is centrifuged to separate the supernatant from the precipitate. When the mutein has been recovered in the supernatant, efficient purification can be achieved in the same manner as the method described by M. Iwane et al. [Biochemical and Biophysical Research Communications, 146, 470–477 (1987)]. When the mutein has been recovered in the precipitate, the precipitate is dissolved in a solution containing a protein denaturant such as guanidine hydrochloride, after which the denaturant concentration is reduced by dialysis or dilution to separate the desired bioactive mutein. The mutein recovered from the precipitate can be prepared as a product of high purity and high activity, like the mutein recovered from the supernatant, by a purification as necessary.

The co-presence of a trace amount of reducing agent during the purification or storage process sometimes serves well to prevent oxidation of the product. However, to cause the Cys residue, newly introduced by amino acid substitution, to form an S—S bond as expected from the steric structure of bFGF, the reducing agent is removed at any time point during the purification process, or purification is conducted without adding the reducing agent.

From the viewpoint of recovery rate and purity, it is preferable that a reducing agent be present during cell disruption through the initial stage of purification, and be removed in the midst of purification. Because said mutein spontaneously forms an S—S bond between some of newly introduced Cys residues or between some of the newly introduced Cys residues and some of existing Cys residues in the absence of reducing agent, the finished purified product, with the reducing agent removed during the purification process, is a mixture of a mutein with S—S bond (oxidized mutein) and a mutein having no S—S bond (reduced mutein). In many cases, the reduced mutein possesses bioactivities similar to those of naturally occurring bFGF, but it is possible to prepare a product mostly comprising the oxidized mutein and accomplish the object of the invention by artificially forming an S—S bond by the method described below.

Examples of methods of forming an S—S bond between two cysteine residues in the molecule include the method based on air oxidation and the method using a glutathione redox buffer [V. P. Saxena and D. B. Wetlaufer, Biochemistry, 9, 5015 (1970)], with preference given to the latter. When a mutein-containing solution and a glutathione redox buffer of appropriate concentration are mixed and kept standing at appropriate temperature, the reduced mutein rapidly turns into the oxidized type. Specifically, it is preferable that the sum of the final concentrations of the oxidized glutathione (abbreviated GSSG) and the reduced glutathione (abbreviated GSH) be in the range from about 0.1 mM to 100 mM, the GSSG-GSH concentration ratio in the range from about 0.05 to 5 and the pH in the range from about 7 to 9; a small amount of EDTA (ethylenediaminetetraacetic acid) may be present concurrently. Although appropriate temperature varies among the muteins, it is preferably between about 4° C. and 40° C. Also, the co-presence of about 1M to 3M urea can increase the efficiency of formation of the desired S—S bond. To terminate the reaction, the pH is reduced to near 6 or the glutathione is removed by dialysis or gel filtration.

For the method based on air oxidation described above, an appropriate buffer, such as Tris-HCl, is added to adjust the mutein-containing solution to a pH of about 7 to 10, preferably about 8 to 9, and the solution is kept standing in contact with air. In this case, the co-presence of about 0.1 $\mu$M to 1 mM ion of a metal such as copper can shorten the time required for S—S bond formation. It is also effective to sparge air or oxygen in the solution to cause gentle bubbling. Any temperature is acceptable, as long as the mutein is not denatured, with preference given to the range from about 0° C. to 40° C.

The S—S bond forming procedure may be conducted at any time point in the mutein purification process, with no limitation on purity or concentration of the mutein.

Since the mutein of the present invention possesses fibroblast growth-promoting activity, vascular endothelial cell growth-promoting activity and angiogenic activity, and has high stability and low toxicity, it can be used as a healing promoting agent for burns, wounds, postoperative tissue healing etc. or as a therapeutic drug for thrombosis, arteriosclerosis and other diseases, based on its angiogenic activity. It can also be used as a reagent for accelerating cell culture.

For pharmaceutical use, the mutein of the present invention can be safely administered orally or non-orally in the form of powder as such, or in the form of pharmaceutical compositions (e.g., injections, tablets, capsules, solutions, ointments) by mixing together with a pharmaceutically acceptable carrier to warm-blooded animals (e.g., humans, mice, rats, hamsters, rabbits, dogs, cats).

The injection is prepared in accordance with a conventional method using physiological saline or an aqueous solution containing glucose and other auxiliaries. Other pharmaceutical compositions, such as tablets and capsules, can also be prepared in accordance with conventional methods.

The carrier for tablets or capsules includes pharmaceutically acceptable carriers (e.g. lactose, corn starch, light silicic anhydride, microcrystalline cellulose, sucrose), binders (e.g. alpha-form starch, methyl cellulose, carboxymethylcellulose, hydroxypropylcellulose, hydroxy polyvinylpyrrolidone), disintegrating agents (e.g. carboxymethylcellulose calcium, starch, low substituted hydroxypropylcellulose), surfactants (e.g. Tween 80 (Kao-Atlas), Pluronic F68 (Asahi Denka, Japan); polyoxyethylene-polyoxypropylene coplymer)), antioxidants (e.g. L-cysteine, sodium sulfite, sodium ascorbate), lubricants (e.g. magnesium stearate, talc).

When the composition is formulated into an injectable aqueous solution, the solution is prepared by conventional methods using a solvent such as an aqueous solvent (e.g., distilled water, physiological saline, Ringer's solution), or oily solvent (e.g., sesame oil, olive oil). If desired, one or more additives may be employed. Such additives include a dissolution aid (e.g. sodium salicylate, sodium acetate), buffer (e.g., sodium citrate, glycerine), isotonizing agent (e.g., glucose, invert sugar), stabilizers (e.g., human serum albumin, polyethylene glycol), preservatiave (e.g., benzyl alcohol, phenol) or analgesics (e.g., benzalkonium chloride, procaine hydrochloride).

Examples of the additives used when the ointments are prepared include vaseline, beweswax, paraffin, liquid paraffin, cholesterol, stearyl alcohol, lanolin, cetyl alcohol and polyethylene glycol.

When using the mutein of the present invention as a pharmaceutical as described above, it is administered to the above-mentioned warm-blooded animals in doses selected as appropriate from the range from about 1 ng to 100 $\mu$g/kg daily, in view of the route of administration, symptoms and other factors.

When using the mutein of the present invention as a reagent for accelerating cell culture, it is preferable to add it to medium to a final concentration of about 0.01 to 10 $\mu$g, more preferably about 0.1 to 10 $\mu$g per liter of medium.

The mutein of the present invention, resulting from substitution of at least one of the amino acids constituting bFGF or an active derivative thereof by cysteine, can serve well as a pharmaceutical, since it has improved stability to acid conditions, heat conditions and so on. Thus, as the mutein of the present invention has a high stability, the mutein can be used as a medicine in a low dosage, the activity of the mutein is maintained for a long period of time, it is easy to handle to make a pharmaceutical preparation and it can be easily to be administered to a living body.

Abbreviations for bases, amino acids and others used in the present specification and drawings attached thereto are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated. Abbreviations are also listed.

DNA: Deoxyribonucleic acid
cDNA: Complementary deoxyribonucleic acid
A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediaminetetraacetic acid
SDS: Sodium dodecyl sulfate
G, Gly: Glycine
A, Ala: Alanine
V, Val: Valine
L, Leu: Leucine
I, Ile: Isoleucine
S, Ser: Serine
T, Thr: Threonine
C, Cys: Cysteine
M, Met: Methionine
E, Glu: Glutamic acid
D, Asp: Aspartic acid
K, Lys: Lysine
R, Arg: Arginine
H, His: Histidine
F, Phe: Phenylalanine
Y, Tyr: Tyrosine
W, Trp: Tryptophan
P, Pro: Proline
N, Asn: Asparagine
Q, Gln: Glutamine
PAGE: Polyacrylamide gel electrophoresis
DMEM: Dulbecco modified Eagle's medium
Tris: Tris (hydroxymethyl) aminomethane
HPLC: High performance liquid chromatography In the present application, the amino acids in the amino acid sequence of human bFGF are numbered on the basis of the N-terminal Pro in the amino acid sequence shown in FIG. 1, which Pro residue is numbered 1. Amino acids in the amino acid sequence of bovine bFGF [Proceedings of the National Academy of Science, USA, 82, 6507 (1985)] are numbered on the basis of the N-terminal Pro, which Pro residue is numbered 1.

Of the transformants produced in the examples below, those having an accession number have been deposited at the Institute for Fermentation, Osaka (IFO) and the Fermentation Research Institute (FRI), Agency of Industrial Science and Technology, Ministry of International Trade and Industry. Their accession numbers and dates of deposition are shown in Table 1 below. In Table 1, the depositions given a FERM BP number are based on the Budapest Treaty.

TABLE 1

| Transformant | IFO | FRI |
| --- | --- | --- |
| E. coli K12MM294 (DE3)/ pLysS, pBFM2 (Example 2) | IFO 15084 (August 28, 1990) | FERM BP-3372 (April 20, 1991) |
| E. coli MM294 (DE3)/ pLysS, pBFM4 (Example 4) | IFO 15276 (March 10, 1992) | FERM BP-3802 (March 18, 1992) |
| E. coli K12MM294 (DE3)/ pLysS, pBFM5 (Example 5) | IFO 15085 (August 28, 1990) | FERM BP-3371 (April 20, 1991) |

EXAMPLE 1

Construction of pUCN23, a plasmid having an NdeI site for site-directed mutagenesis (1) Insertion of cDNA of hbFGF mutein CS23 into the plasmid vector pUC118B A 0.5 kbp DNA fragment containing a cDNA of CS23 was obtained by digestion with restriction enzymes EcoRI and PstI from the phage vector M13mp8, incorporating a cDNA of the human bFGF mutein CS23 resulting from substitution of the 69- and 87-position Cys of human bFGF by Ser [M. Seno et al., Biochemical and Biophysical Research Communications, 151, 701–708 (1988)] (hereinafter also abbreviated CS23). Next, the vector pUC118B, prepared by converting the HindIII site in the multicloning region of pUC118, a plasmid vector for preparing single-stranded chain, to a BglII site by site-directed mutagenesis (pUC118B is described as pTB891 in Japanese Patent Application Laid-open No. 2-209894/1990 which corresponds to EP-A-326, 907), was digested with EcoRI and PstI. The resulting fragment was ligated to the above-mentioned DNA fragment containing the CS23 gene, using T4 DNA ligase. The resulting DNA ligation product was used to transform *Escherichia coli* MV1184. The resulting transformant cells were seeded over plates containing Xgal as the indicator, and then a white colony containing pUCB23, a recombinant plasmid resulting from accurate insertion of the CS23 gene into pUC118B, was selected. The clone thus obtained, when infected with the helper phage KO7, released in the medium single-stranded pUCB23 containing the plus strand of DNA which codes for the hbFGF mutein CS23, in the form of phage particles. This single-stranded DNA was purified and used as a template for site-directed mutagenesis. *Escherichia coli* MV1184 and the helper phage KO7, used here, are described by J. Vieira and J. Messing in Methods in Enzymology, 153, 3–11 (1987).

(2) Conversion of restriction enzyme EcoRI site to NdeI site

A method using the phage T7 RNA polymerase is known to serve well in the mass expression of foreign genes in *Escherichia coli* cells [F. W. Studier and B. A. Moffatt, Journal of Molecular Biology, 189, 113–130 (1986)]. For inserting the desired gene into pET3c, the expression plasmid used for this method, it is advantageous to have a restriction enzyme NdeI site in the upstream of the gene. To convert the EcoRI site in the immediate upstream of the translational initiation codon of the CS23 gene of pUCB23 obtained in (1) to an NdeI site, the following oligonucleotide 1: 5'-TGCTGG<u>CATATG</u>ATTCGTAATC-3'(SEQ ID NO: 5)

Figure 3:
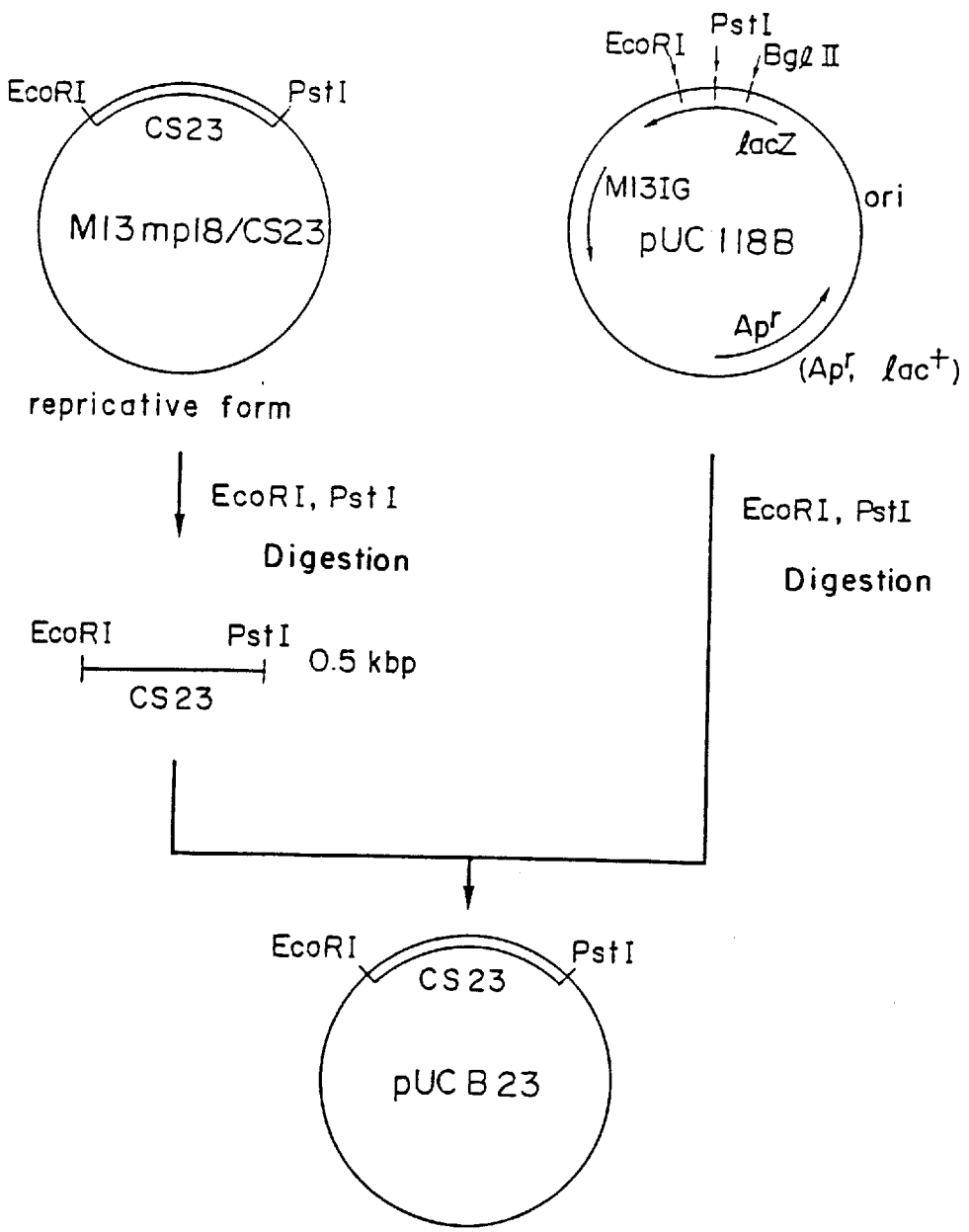
FIG. 3 is a construction scheme of the plasmid pUCB23 obtained in Example 1.
Figure 4:
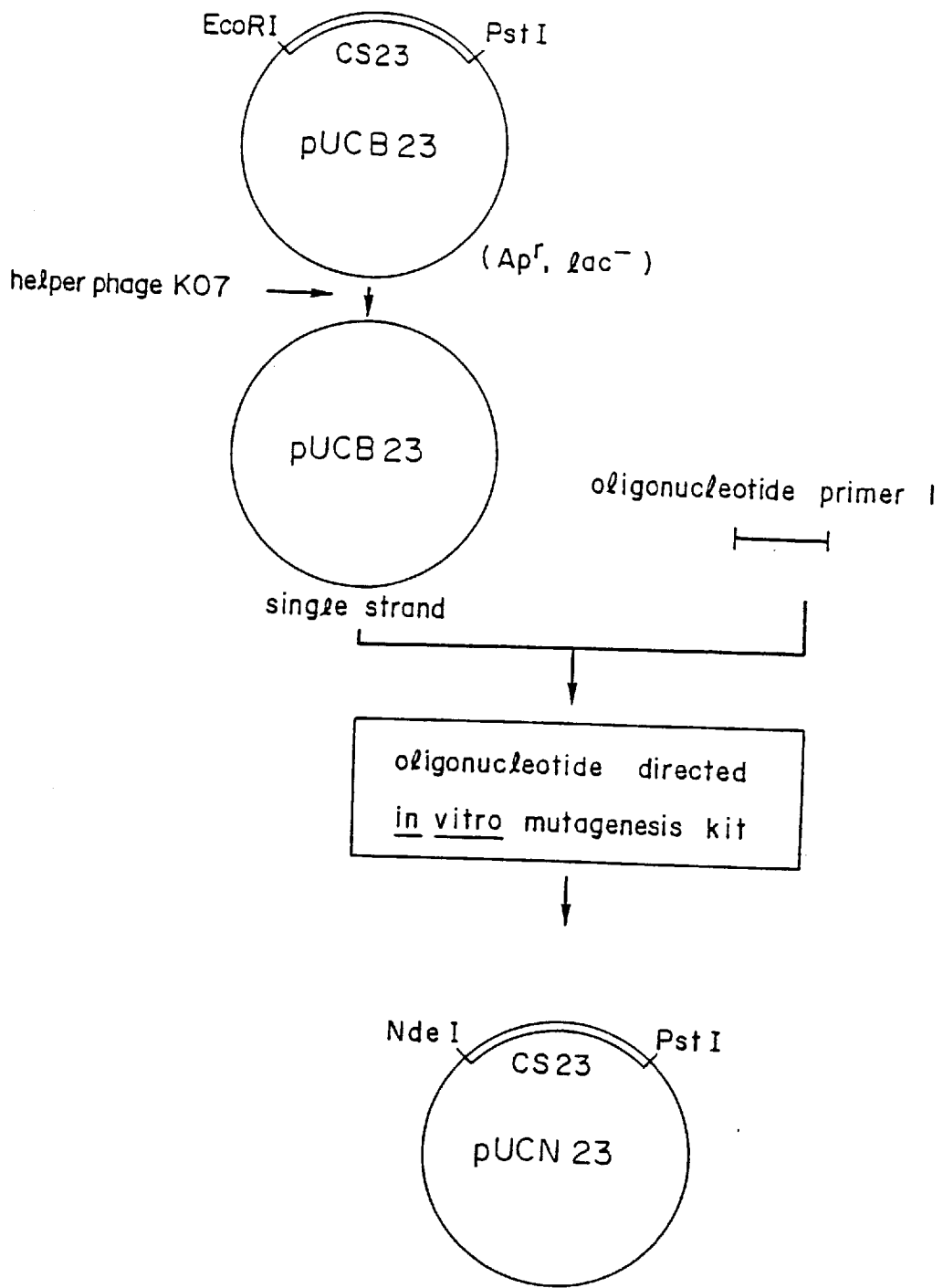
FIG. 4 is a construction scheme of the plasmid pUCN23 obtained in Example 1.

NdeI was synthesized (FIG. 2(*a*)). 50 pmol of this oligonucleotide was kept standing at 37° C. in the presence of 1 mM ATP, 50 mM Tris-hydroxymethylaminomethane hydrochloride (pH 8.0), 10 mM $MgCl_2$, 5 mM dithiothreitol (DTT) and 10 units of T4 kinase for 30 minutes to phosphorylate its 5'-OH terminal. With 4 pmol of this product in combination with 5 μg of the single-stranded chain pUCB23 prepared to contain the CS23 gene in (1) above for use as a template, mutation was induced using the Oligonucleotide-Directed In Vitro Mutagenesis System, Version 2 (a kit for site-directed mutagenesis produced by Amersham). The resulting double-stranded cyclic DNA was used to transform *Escherichia coli* MV1184 to yield a large number of clones. After some of these clones were cultivated in 3 ml of a double-concentrated YT medium at 37° C. for 15 hours, the plasmid DNA was purified, and a clone was selected which yields no fragment even by digestion with the restriction enzymes EcoRI and BamHI, but yields a fragment by digestion with NdeI and BamHI. The plasmid pUCN23, resulting from conversion of the EcoRI site to an NdeI site in pUCB23, was thus obtained (FIGS. 3 and 4).

Example 2

Production of gene which codes for mutein BFM2 and its expression in *Escherichia coli*

Detailed observation of the three-dimensional structures of human bFGF and the hbFGF mutein CS23 revealed the presence of the side chain of the 118-position Leu residue in the vicinity of the side chain of the 25-position Cys residue. The inventors therefore considered it possible to allow the 25-position Cys to form a disulfide bond with the 118-position residue by replacing the 118-position Leu with Cys. The mutein resulting from conversion of the 118-position Leu to Cys was named BFM2. The method of producing its gene and its expression in *Escherichia coli* are described below.

(1) Production of gene which codes for mutein BFM2

First, to convert the codon of the 118-position Leu to the codon of Cys, the following oligonucleotide 2:

5'-CAGTTCGTTT<u>GCATGC</u>CACATAC-3'(SEQ ID NO: 1)

SphI was synthesized (FIG. 2(*b*)). Using this synthetic oligonucleotide (4 pmol), whose 5'-OH terminal was previously phosphorylated by T4 kinase treatment, and the single-stranded pUCN23 (5 μg) prepared in Example 1 (2), a mutated plasmid was obtained using the site-directed mutagenesis kit described in Example 1. The resulting plasmid was used to transform *Escherichia coli* MV1184, which was then seeded on an agar plate of a double-concentrated YT medium containing 150 μg/ml ampicillin and cultivated at 37° C. for 15 hours to yield a large number of colonies. From 6 of these colonies, a small amount of cells was collected and cultivated in 0.3 ml of a double-concentrated YT medium about 5 hours. 30 μl of this culture broth and 30 μl of a solution containing the helper phage KO7 were mixed and kept standing at 37° C. for 1 hour, followed by overnight cultivation in the presence of 3 ml of double-concentrated YT medium. The culture broth was centrifuged to separate the supernatant from the cells. From the cells, the plasmid was crudely purified by the alkalilysis method; from the supernatant, a single-stranded DNA in the form of phage particles was recovered by a conventional method.

The oligonucleotide 2 contains a restriction enzyme SphI recognition site, not present in the gene which codes for the hbFGF mutein CS23, to serve as a template.

Consequently, when the correctly mutated plasmid is reacted with SphI, a 121 bp fragment should occur as a result of cleavage at two sites, namely the SphI site newly formed by mutation and the original SphI site in the multicloning region of pUC118B. The plasmids obtained from the six colonies described above were digested with SphI and analyzed by agarose gel electrophoresis; the presence of correct-sized fragments in two clones was confirmed.

Using the single-stranded plasmids of these two clones as templates, the base sequences were analyzed by the dideoxy method; induction of the desired mutation was confirmed.

Figure 5:
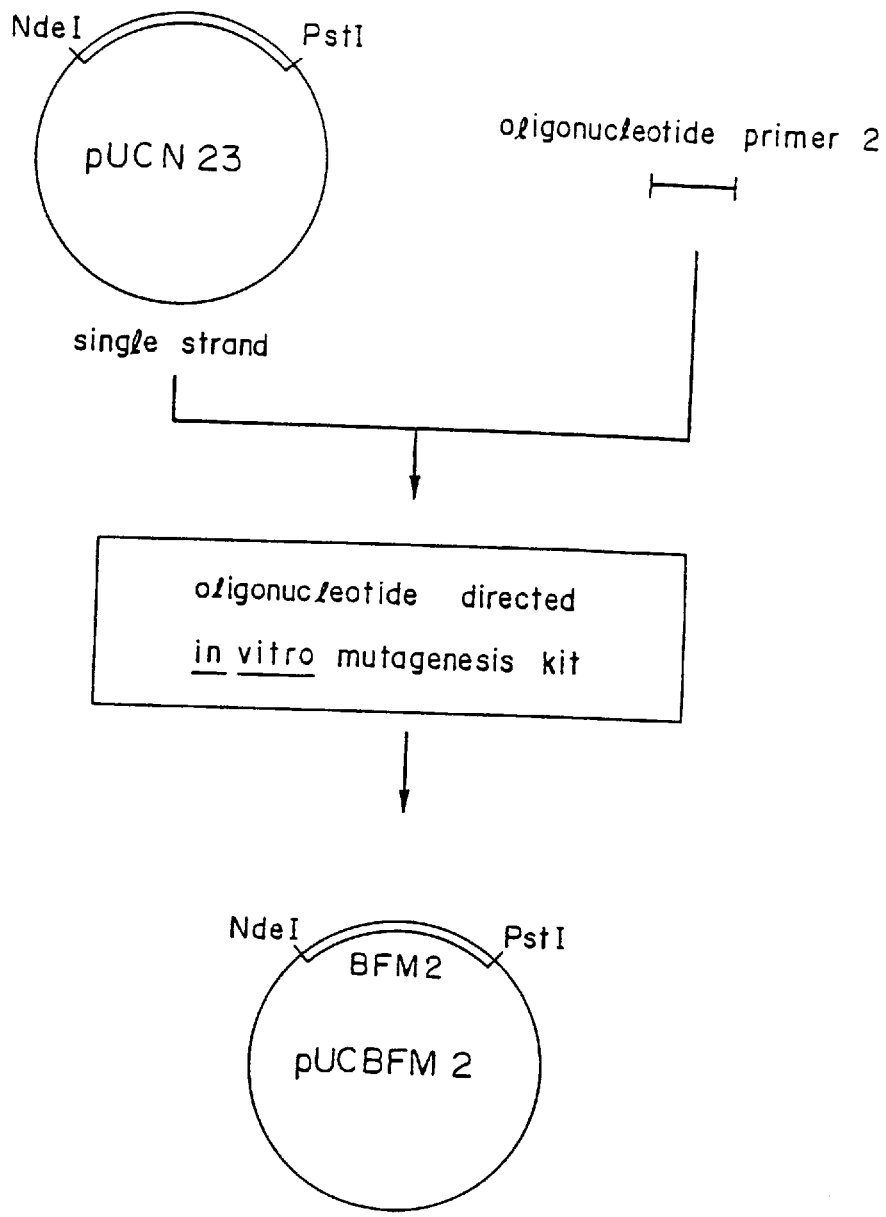
FIG. 5 is a construction scheme of the plasmid pUCBFM2 obtained in Example 2.

The thus-obtained plasmid containing the gene which codes for BFM2 was named pUCBFM2 (FIG. 5).

(2) Construction of plasmid pBFM2 for expression in *Escherichia coli*

Figure 6:
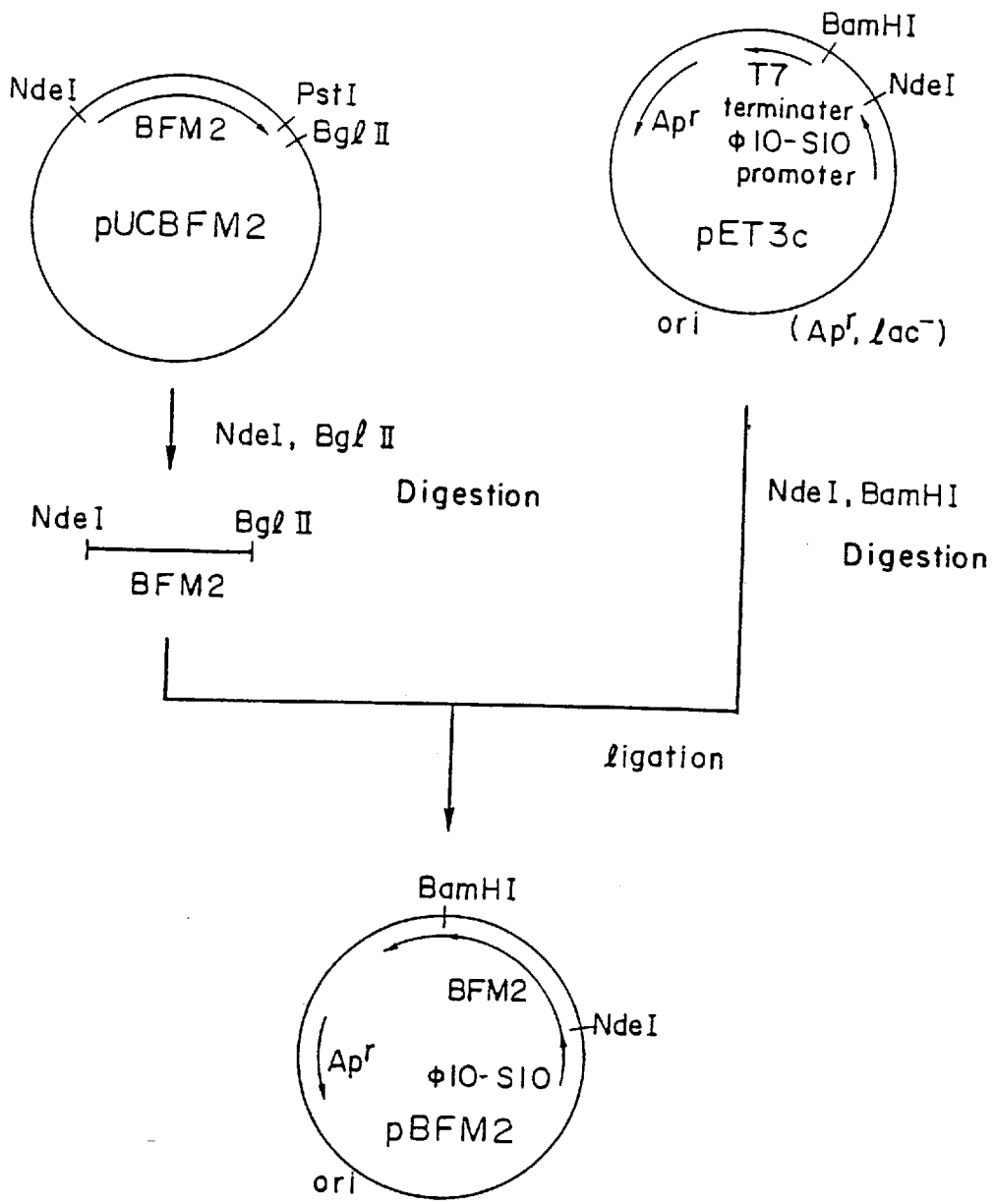
FIG. 6 is a construction scheme of the plasmid pBFM2 obtained in Example 2.

The plasmid pUCBFM2 obtained in (1) was digested with restriction enzymes NdeI and BglII to yield an about 0.5 kbp fragment which codes for the mutein BFM2. After purification by agarose gel electrophoresis, this fragment was ligated to the expression plasmid vector pET3c [F. W. Stadier et al., Methods in Enzymology, 195, 60–89 (1990)], previously digested with restriction enzymes NdeI and BamHI, by T4 ligase. In this case, the cohesive end resulting from BglII digestion of the DNA fragment which codes for the mutein and the cohesive end resulting from BamHI digestion of pET3c are perfectly mutually complementary; the desired cyclic DNA should emerge by ligase treatment. It should be noted, however, that neither restriction enzyme can cause cleavage after ligation of the BglII and BamHI sites. The expression plasmid thus obtained was named pBFM2 (FIG. 6).

The λ phage DE3 [F. W. Stadier et al., Journal of Molecular Biology, 189, 113–130 (1986)], incorporating the RNA polymerase gene of T7 phage, was lysogenized to *Escherichia coli* MM294 strain, followed by introduction of the plasmid pLysS [F. W. Stadier et al., Journal of Molecular Biology, 189, 113–130 (1986)], having the lysozyme gene of T7 phage, to yield *Escherichia coli* MM294(DE3)/pLysS strain.

The plasmid pBFM2 was used to transform *Escherichia coli* MM294(DE3)/pLysS to yield *E. coli* MM294(DE3)/pLysS, pBFM2 (IFO 15084, FERM BP-3372), a transformant having a plasmid containing the mutein-encoding gene shown in FIG. 7.

(3) Expression of mutein BFM2

Cells of the thus-obtained transformant *Escherichia coli* MM294(DE3)/pLysS, pBFM2 were cultivated overnight in 3 ml of an LB medium containing 35 µg/ml ampicillin and 10 µg/ml chloramphenicol. A 2.5 ml portion of this culture broth was added to 50 ml of the same medium (containing 35 µg/ml ampicillin, 10 µg/ml chloramphenicol) and cultivated at 37° C. for 2 hours. When the Klett value reached 130, isopropyl βD-galactopyranoside (IPTG) was added to reach a final concentration of 0.3 mM, followed by additional 3 hours of cultivation. Before IPTG addition and after 3 hours of cultivation, an aliquot of the culture broth was centrifuged. Cells were collected and analyzed by sodium dodecyl sulfate polyacrylamide gel electrophoresis (SDS-PAGE) under reducing conditions; induction of expression of the mutein BFM2 by the addition of IPTG was confirmed. Also, immunoblotting confirmed that the expressed protein binds specifically to the anti-bFGF antibody [M. Seno et al., Hybridoma, 8, 209–221 (1989)].

(4) FGF activity of cell extract

The cells caused to express the mutein in (2) above were suspended in a 0° C. buffer containing 10% sucrose, 20 mM Tris-HCl (pH 7.4), 10 mM EDTA, 0.2M NaCl and 1 mM phenylmethylsulfonyl fluoride (PMSF). To this suspension was added lysozyme to a final concentration of 0.1 mg/ml; this mixture was kept standing at 0° C. for 30 to 45 minutes, followed by 30 seconds of sonication. This solution was centrifuged at a centrifugal force of about 20,000 g for 30 minutes; the resulting supernatant was used as a cell extract.

Mouse BALB/c3T3 cells were seeded and cultivated on 96-well microtiter plates (flat-based) containing a DMEM medium containing 5% fetal calf serum, at a density of $2 \times 10^3$ cells per well. On the following day, the medium was replaced with a DAEM medium containing 0.5% fetal calf serum. After 3 days of cultivation, 10 µl of each of a series of dilutions, diluted in 5-fold steps (50 to 500 folds) of the above-mentioned cell extract with a DMEM medium containing 0.5% BSA, was added to the cell culture broth. After cultivation for further 18 more hours, 2 µl of $^3$H-Tdr (5 Ci/mmol, 0.5 mCi/ml, RCC Amersham) was added to each well. After 6 hours, the culture broth was totally replaced with phosphate-buffered saline (PBS) to wash the cells. After the PBS was aspirated, 100 µl of 5% SDS solution was added. The mixture was kept standing overnight at 37° C. to completely lyse the cells, after which the amount of $^3$H-Tdr taken into the cells was estimated by liquid scintillation counter for an index of the cell growth-promoting activity of FGF. As a standard, bovine pituitary derived FGF (Takara Shuzo, Japan) was used.

The extract from *E. coli* MM294(DE3)/pLys, pBFM2 was found to possess FGF activity.

A mutein having the amino acid sequence shown in FIG. 7, resulting from replacement of the 69-position Cys and the 87-position Cys by Ser and the 118-position Leu by Cys in human bFGF, was thus obtained.

EXAMPLE 3

Production of gene which codes for mutein BFM3 and its expression in *Escherichia coli*

Detailed observation of the three-dimensional structures of human bFGF and the human bFGF mutein CS23 revealed the presence of the side chain of the 139-position Phe residue in the vicinity of the side chain of the 25-position Cys residue. The inventors therefore considered it possible to allow the 139-position residue to form a disulfide bond with the 25-position Cys by replacing the 139-position Phe by Cys. The mutein resulting from conversion of the 139-position Phe to Cys was named BFM3. The method of producing its gene and its expression in *Escherichia coli* are described below.

(1) Production of gene which codes for mutein BFM3

First, to convert the codon of the 139-position Phe to the codon of the Cys, the following oligonucleotide 3:

5'-CATTGGAAGACAAAGTATAGC-3' (SEQ ID NO: 2)

was synthesized (FIG. 2(c)). Using this synthetic oligonucleotide (4 pmol), whose 5'-OH terminal was previously phosphorylated by T4 kinase treatment, and the single-stranded pUCN23 (5 µg) prepared in Example 1 (2), a mutated plasmid was obtained using the site-directed mutagenesis kit described in Example 1. The resulting plasmid was used to transform *Escherichia coli* MV1184. Cells of the resulting transformant were seeded on an agar plate of a double-concentrated YT medium containing 150 µg/ml ampicillin and cultivated at 37° C. for 15 hours to yield a large number of colonies. From 3 of these colonies, a small amount of cells was collected and cultivated in 0.3 ml of double-concentrated YT medium for about 5 hours. 30 µl of this culture broth and 30 µl of a solution containing the helper phage KO7 were mixed and kept standing at 37° C. for 1 hour, followed by overnight cultivation in the presence of 3 ml of double-concentrated YT medium. The culture broth was centrifuged to separate the supernatant from the cells. From the cells, the plasmid was crudely purified by the alkalilysis method; from the supernatant, the single-stranded DNA in the form of phage particles was recovered by a conventional method.

Using the single-stranded plasmid as a template, the base sequence was analyzed by the dideoxy method; a single clone incorporating the desired mutation was thus identified.

Figure 8:
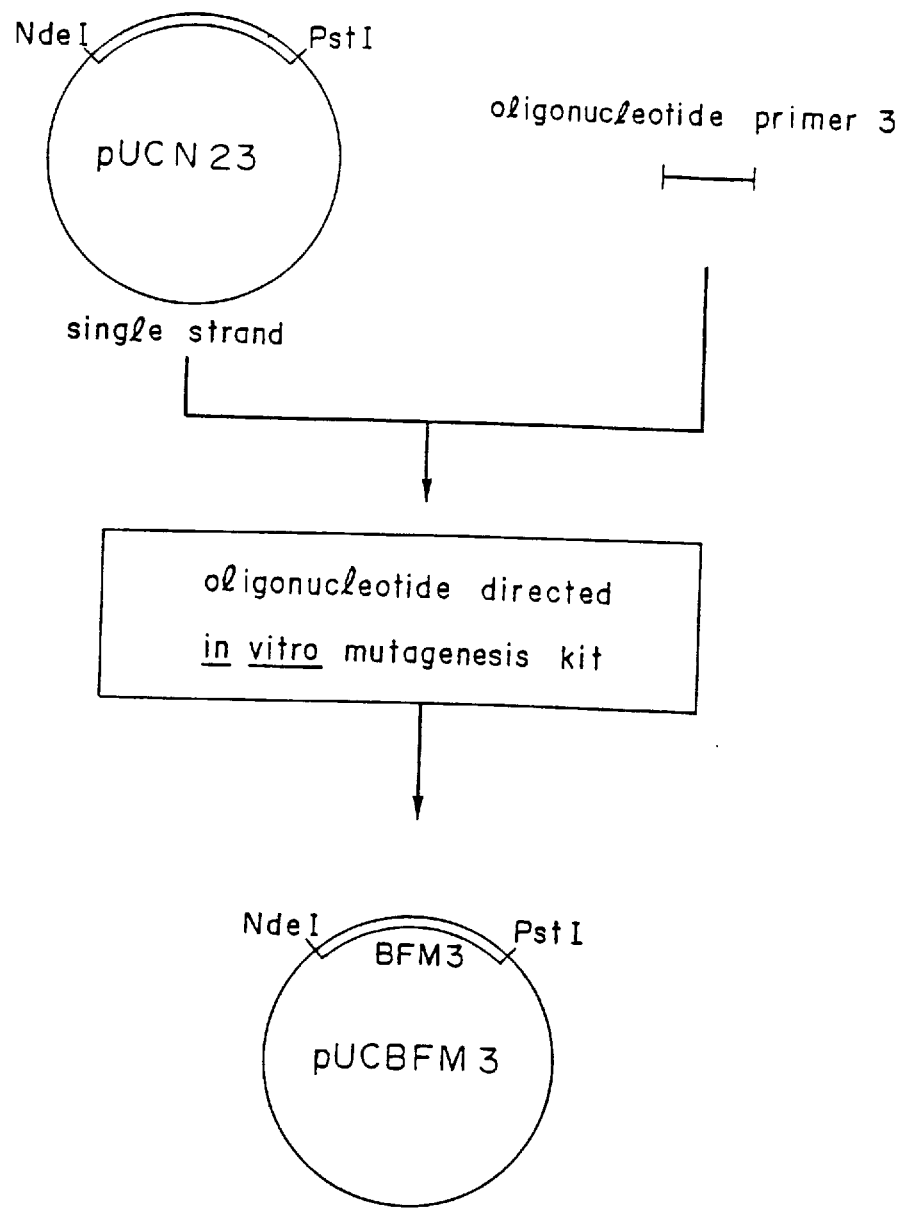
FIG. 8 is a construction scheme of the plasmid pUCBFM3 obtained in Example 3.

The thus-obtained plasmid containing the BFM3-encoding gene was named pUCBFM3 (FIG. 8).

(2) Construction of plasmid pBFM3 for expression in *Escherichia coli*

Figure 9:
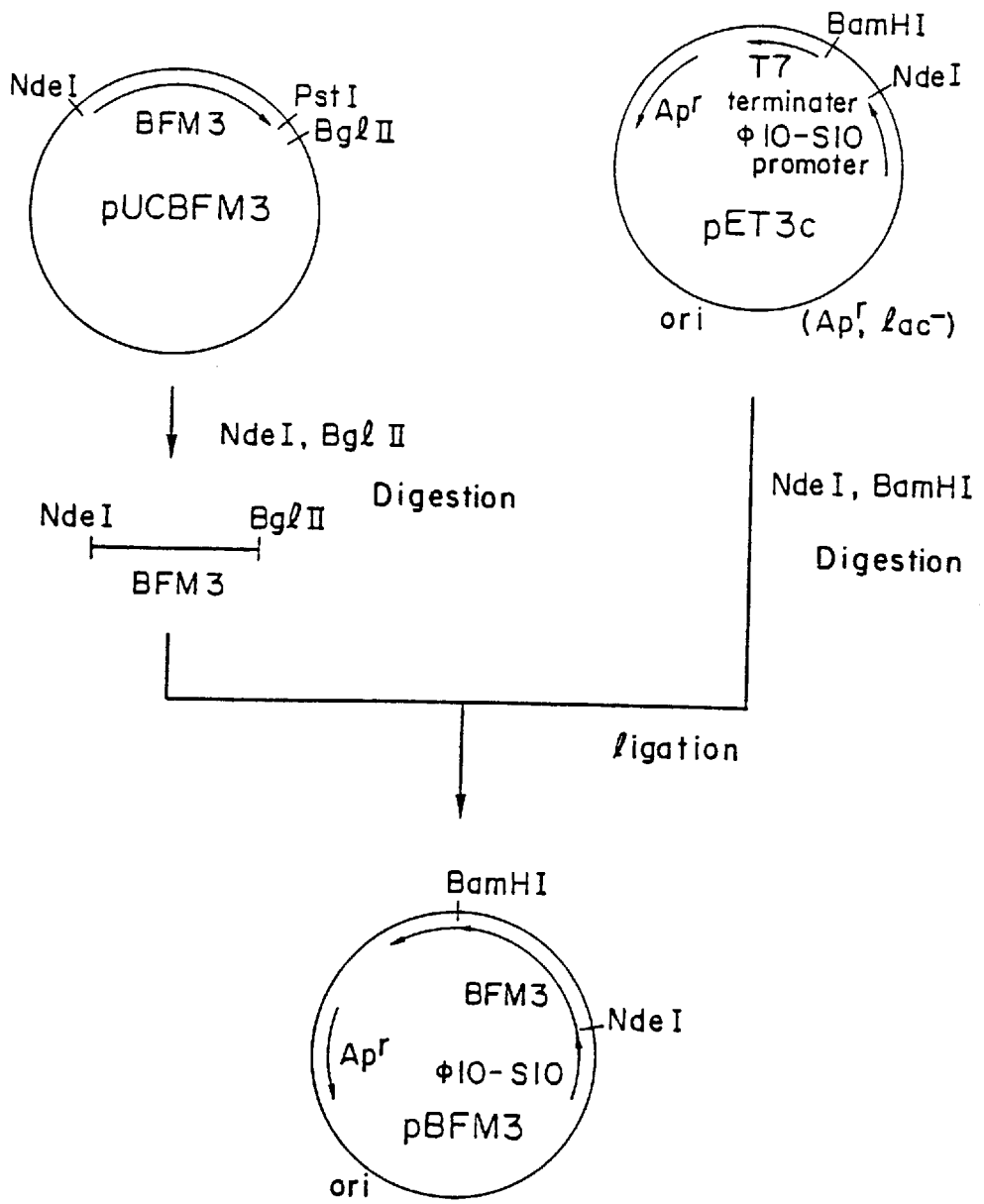
FIG. 9 is a construction scheme of the plasmid pBFM3 obtained in Example 3.

The plasmid pUCBFM3 obtained in (1) was digested with restriction enzymes NdeI and BglII to yield an about 0.5 kbp fragment which codes for the mutein BFM3. After purification by agarose gel electrophoresis, this fragment was ligated to the expression plasmid vector pET3c [F. W. Stadier et al., Methods in Enzymology, 195, 60–89 (1990)], previously digested with restriction enzymes NdeI and BamHI, using T4 ligase. In this case, the cohesive end resulting from BglII digestion of the DNA fragment which codes for the mutein and the cohesive end resulting from BamHI digestion of pET3c are perfectly mutually complementary; the desired cyclic DNA should emerge by ligase treatment. It should be noted, however, that neither restriction enzyme can cause cleavage after ligation of the BglII and BamHI sites. The expression plasmid thus obtained was named pBFM3 (FIG. 9).

The plasmid pBFM3 was used to transform *Escherichia coli* MM294(DE3)/pLysS to yield *E. coli* MM294(DE3)/pLysS, pBFM3 a transformant having a plasmid containing the mutein-encoding gene shown in FIG. 10.

(3) Expression of mutein BFM3

Figure 17:
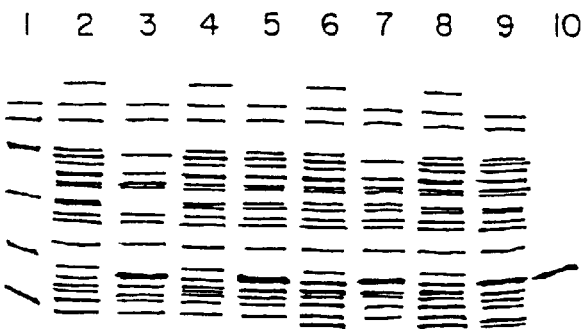
FIG. 17 shows the results of SDS-PAGE obtained before and after the expressions of the muteins in Examples 2 (2), 3 (2), 4 (2) and 5 (2). Lanes 1 through 10 in FIG. 17 denote the following.

*Escherichia coli* MM294(DE3)/pLysS, pBFM3 was cultivated overnight in 3 ml of an LB medium containing 35 µg/ml ampicillin and 10 µg/ml chloramphenicol. A 2.5 ml portion of this culture broth was added to 50 ml of the same medium (containing 35 μg/ml ampicillin, 10 μg/ml chloramphenicol) and cultivated at 37° C. for 2 hours. When the Klett value reached 130, isopropyl βD-galactopyranoside (IPTG) was added to reach a final concentration of 0.3 mM, followed by 3 additional hours of cultivation. Before IPTG addition and after 3 hours of cultivation, an aliquot of the culture broth was centrifuged. Cells were collected and analyzed by sodium dodecyl sulfate polyacrylamide gel electrophoresis (SDS-PAGE) under reducing conditions; induction of expression of the mutein BFM3 by the addition of IPTG was confirmed (FIG. 17). Also, immunoblotting confirmed that the expressed protein binds specifically to the anti-bFGF antibody [M. Seno et al., Hybridoma, 8, 209–221 (1989)]. (FIG. 18)

(4) FGF activity of cell extract

From the cells caused to express the mutein as described in (2) above, a cell extract was prepared by the method described in Example 2 (3), followed by determination of FGF activity by the method described in Example 2 (4). As a result, the extract of the bacterial cell MM294(DE3)/pLys, pBFM3 was found to possess FGF activity.

A mutein having the amino acid sequence shown in FIG. 10, resulting from replacement of the 69-position Cys and the 87-position Cys by Ser and the 139-position Phe by Cys in human bFGF, was thus obtained.

EXAMPLE 4

Production of gene which codes for mutein BFM4 and its expression in *Escherichia coli*

Detailed observation of the three-dimensional structures of human bFGF and the human bFGF mutein CS23 revealed the presence of the side chain of the 75-position Ala residue in the vicinity of the side chain of the 92-position Cys residue. The inventors therefore considered it possible to allow the 75-position residue to form a disulfide bond with the 92-position Cys by replacing the 75-position Ala with Cys. The mutein resulting from conversion of the 75-position Ala to Cys was named BFM4. The method of producing its gene and its expression in *Escherichia coli* are described below.

(1) Production of gene which codes for mutein BFM4

First, to convert the codon of the 75-position Ala to the codon of Cys, the following oligonucleotide 4:

5'-TTCCTTCATACACAGGTAACGA-3' (SEQ ID NO: 3)

was synthesized (FIG. 2(d)). Using this synthetic oligonucleotide (4 pmol), whose 5'-OH terminal was previously phosphorylated by T4 kinase treatment, and the single-stranded pUCN23 (5 μg) prepared in Example 1 (2), a mutated plasmid was obtained using the site-directed mutagenesis kit described in Example 1. The resulting plasmid was used to transform *Escherichia coli* MV1184. Cells of the resulting transformant were seeded on an agar plate of a double-concentrated YT medium containing 150 μg/ml ampicillin and cultivated at 37° C. for 15 hours to yield a large number of colonies. From 6 of these colonies, a small amount of cells was collected and cultivated in 0.3 ml of double-concentrated YT medium for about 5 hours. 30 μl of this culture broth and 30 μl of a solution containing the helper phage KO7 were mixed and kept standing at 37° C. for 1 hour, followed by overnight cultivation in the presence of 3 ml of double-concentrated YT medium. The culture broth was centrifuged to separate the supernatant from the cells. From the cells, the plasmid was crudely purified by the alkalilysis method; from the supernatant, single-stranded DNA in the form of phage particles was recovered by a conventional method.

Using the single-stranded plasmid as templates, the base sequences were analyzed by the dideoxy method; three clones incorporating the desired mutation were thus identified.

Figure 11:
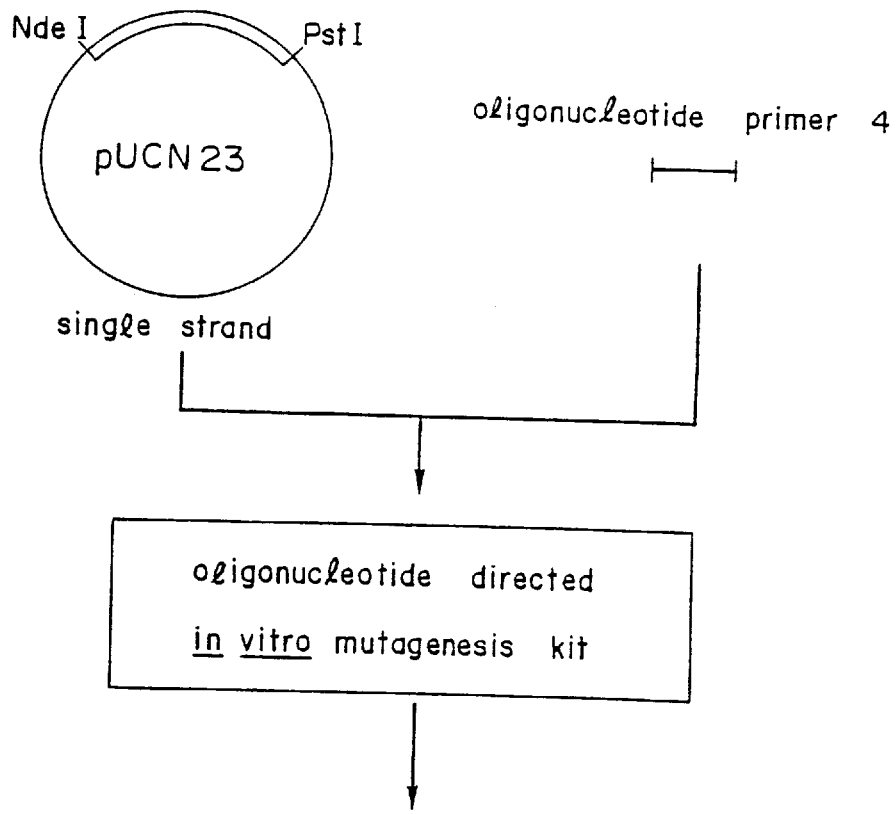
FIG. 11 is a construction scheme of the plasmid pUCBFM4 obtained in Example 4.

The thus-obtained plasmid containing the BFM4-encoding gene was named pUCBFM4 (FIG. 11).

(2) Construction of plasmid pBFM4 for expression in *Escherichia coli*

Figure 12:
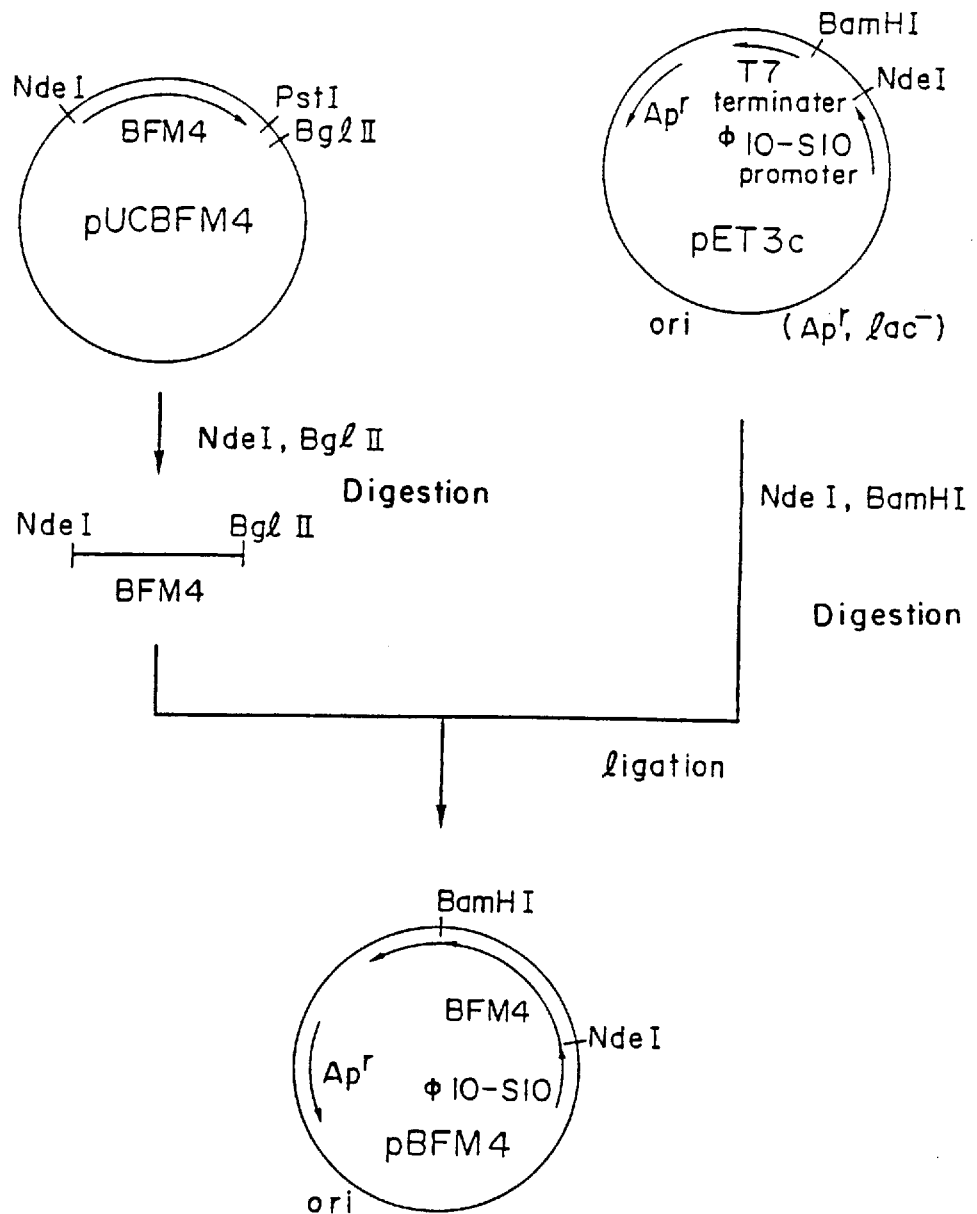
FIG. 12 is a construction scheme of the plasmid pBFM4 obtained in Example 4.

The plasmid pUCBFM4 obtained in (1) was digested with restriction enzymes NdeI and BglII to yield an about 0.5 kbp fragment which codes for the mutein BFM4. After purification by agarose gel electrophoresis, this fragment was ligated to the expression plasmid vector pET3c [F. W. Stadier et al., Methods in Enzymology, 195, 60–89 (1990)], previously digested with restriction enzymes NdeI and BamHI, by T4 ligase. In this case, the cohesive end resulting from BglII digestion of the mutein-encoding DNA fragment and the cohesive end resulting from BamHI digestion of pET3c are perfectly mutually complementary; the desired cyclic DNA should emerge by ligase treatment. It should be noted, however, that neither restriction enzyme can cause cleavage after ligation of the BglII and BamHI sites. The expression plasmid thus obtained was named pBFM4 (FIG. 12).

The plasmid pBFM4 was used to transform *Escherichia coli* MM294(DE3)/pLysS to yield *E. coli* MM294(DE3)/pLysS, pBFM4 (IFO 15276, FERM BP-3802), a transformant having a plasmid containing the mutein-encoding gene shown in FIG. 13.

(3) Expression of mutein BFM4

Cells of the transformant *Escherichia coli* MM294(DE3)/pLysS, pBFM4 were cultivated in 3 ml of an LB medium containing 35 μg/ml ampicillin and 10 μg/ml chloramphenicol overnight. A 2.5 ml portion of this culture broth was added to 50 ml of the same medium (containing 35 μg/ml ampicillin, 10 μg/ml chloramphenicol) and cultivated at 37° C. for 2 hours. When the Klett value reached 130, isopropyl βD-galactopyranoside (IPTG) was added to reach a final concentration of 0.3 mM, followed by additional 3 hours of cultivation. Before IPTG addition and after 3 hours of cultivation, an aliquot of the culture broth was centrifuged. Cells were collected and analyzed by sodium dodecyl sulfate polyacrylamide gel electrophoresis (SDS-PAGE) under reducing conditions; induction of expression of the mutein BFM4 by the addition of IPTG was confirmed (FIG. 17). Also, immunoblotting confirmed that the expressed protein binds specifically to the anti-bFGF antibody [M. Seno et al., Hybridoma, 8,209–221 (1989)] (FIG. 18).

(4) FGF activity of cell extract

From the cells caused to express the mutein as described in (2) above, a cell extract was prepared by the method described in Example 2 (3), followed by determination of FGF activity by the method described in Example 2 (4). The extract from cells of MM294(DE3)/pLys, pBFM4 was found to possess FGF activity.

A mutein having the amino acid sequence shown in FIG. 12, resulting from replacement of the 69-position Cys and the 87-position Cys by Ser and the 75-position Ala by Cys in human bFGF, was thus obtained.

EXAMPLE 5

Production of gene which codes for mutein BFM5 and its expression in *Escherichia coli*

Detailed observation of the three-dimensional structures of human bFGF and the human bFGF mutein CS23 revealed the presence of the side chain of the 85-position Ser residue in the vicinity of the side chain of the 92-position Cys residue. The inventors therefore considered it possible to allow the 85-position residue to form a disulfide bond with the 92-position Cys by replacing the 85-position Ser with Cys. The mutein resulting from conversion of the 85-position Ser to Cys was named BFM5. The method of producing its gene and its expression in *Escherichia coli* are described below.

(1) Production of gene which codes for mutein BFM5

First, to convert the codon of the 85-position Ser to the codon of Cys, the following oligonucleotide 5:

5'-AACAGACTT<u>GCATGC</u>TAGTAATCT-3'(SEQ ID NO: 4)
        SphI was synthesized (FIG. 2(e)). Using this synthetic oligonucleotide (4 pmol), whose 5'-OH terminal was previously phosphorylated by T4 kinase treatment, and the single-stranded pUCN23 (5 μg) prepared in Example 1 (2), a mutated plasmid was obtained using the site-directed mutagenesis kit described in Example 1. The resulting plasmid was used to transform *Escherichia coli* MV1184. Cells of the resulting transformant were seeded on an agar plate of a double-concentrated YT medium containing 150 μg/ml ampicillin and cultivated at 37° C. for 15 hours to yield a large number of colonies. From 6 of these colonies, a small amount of cells was collected and cultivated for about 5 hours in 0.3 ml of double-concentrated YT medium. 30 μl of this culture broth and 30 μl of a solution containing the helper phage KO7 were mixed and kept standing at 37° C. for 1 hour, followed by overnight cultivation in the presence of 3 ml of double-concentrated YT medium. The culture broth was centrifuged to separate the supernatant from the cells. From the cells, the plasmid was crudely purified by the alkali method; from the supernatant, the single-stranded DNA in the form of phage particles was recovered by a conventional method.

The oligonucleotide 5 contains a restriction enzyme SphI recognition site, not present in the gene, which codes for the hbFGF mutein CS23 to serve as a template.

Consequently, when the correctly mutated plasmid is reacted with SphI, a 220 bp fragment should occur as a result of cleavage at two sites, namely the SphI site newly formed by mutation and the original SphI site in the multicloning region of pUC118B. The plasmids obtained from the 6 colonies described above were digested with SphI and analyzed by agarose gel electrophoresis; the presence of a correctly located fragment was confirmed in two clones.

Using the single-stranded plasmids of these two clones as templates, the base sequences were analyzed by the dideoxy method; the clones were found to incorporate the desired mutation.

Figure 14:
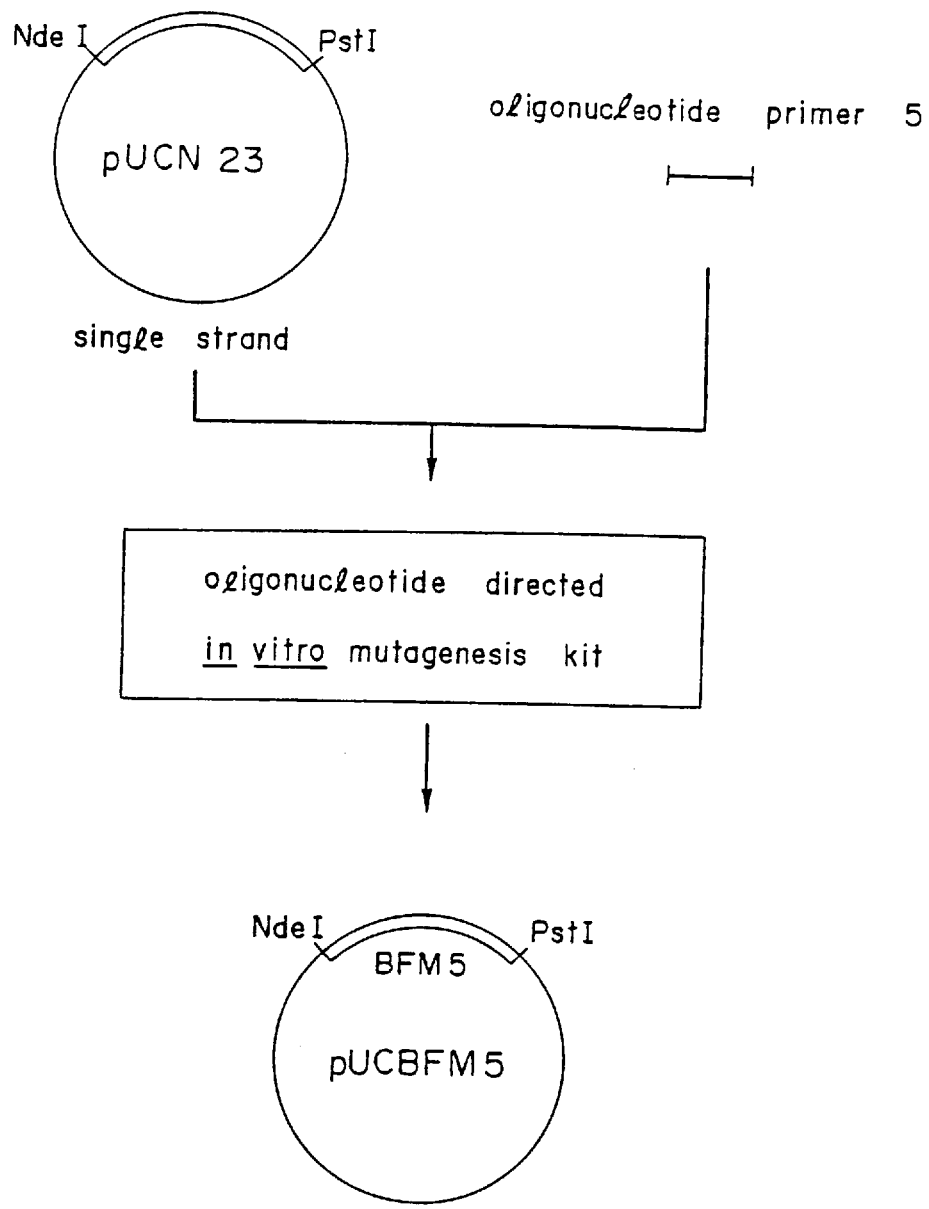
FIG. 14 is a construction scheme of the plasmid pUCBFM5 obtained in Example 5.

The thus-obtained plasmid containing the BFM5-encoding gene was named pUCBFM5 (FIG. 14).

(2) Construction of plasmid pBFM5 for expression in *Escherichia coli*

Figure 15:
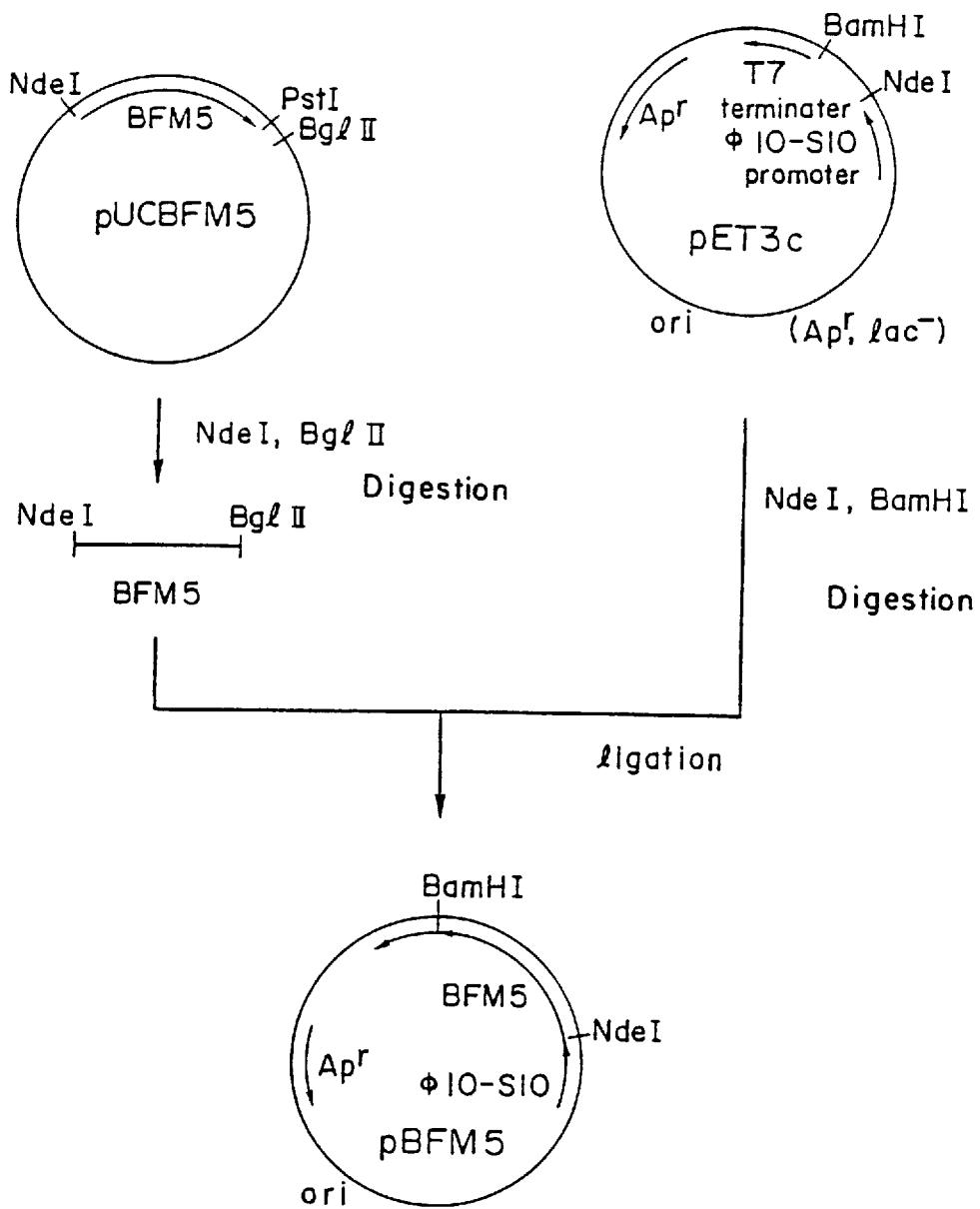
FIG. 15 is a construction scheme of the plasmid pBFM5 obtained in Example 5.

The plasmid pUCBFM5 obtained in (1) was digested with restriction enzymes NdeI and BglII to yield an about 0.5 kbp fragment which codes for the mutein BFM5. After purification by agarose gel electrophoresis, this fragment was ligated to the expression plasmid vector pET3c [F. W. Stadier et al., Methods in Enzymology, 195, 60–89 (1990)], previously digested with restriction enzymes NdeI and BamHI, using T4 ligase. In this case, the cohesive end resulting from BglII digestion of the mutein-encoding DNA fragment and the cohesive end resulting from BamHI digestion of pET3c are perfectly mutually complementary; the desired cyclic DNA should emerge by ligase treatment. It should be noted, however, that neither restriction enzyme can cause cleavage after ligation of the BglII and BamHI sites. The expression plasmid thus obtained was named pBFM5 (FIG. 15).

The plasmid pBFM5 was used to transform *Escherichia coli* MM294(DE3)/pLysS to yield *E. coli* MM294(DE3)/pLysS, pBFM5 (IFO 15085, FERM BP-3371), a transformant having a plasmid containing the mutein-encoding gene shown in FIG. 16.

(3) Expression of mutein BFM5

Cells of the thus-obtained transformant *Escherichia coli* MM294(DE3)/pLysS, pBFM5 were cultivated overnight in 3 ml of an LB medium containing 35 μg/ml ampicillin and 10 μg/ml chloramphenicol. A 2.5 ml portion of this culture broth was added to 50 ml of the same medium (containing 35 μg/ml ampicillin, 10 μg/ml chloramphenicol) and cultivated at 37° C. for 2 hours. When the Klett value reached 130, isopropyl βD-thiogalactopyranoside (IPTG) was added to reach a final concentration of 0.3 mM, followed by further 3 hours of cultivation. Before IPTG addition and after 3 hours of cultivation, an aliquot of the culture broth was centrifuged. Cells were collected and analyzed by sodium dodecyl sulfate polyacrylamide gel electrophoresis (SDS-PAGE) under reducing conditions; induction of expression of the mutein BFM5 by the addition of IPTG was confirmed (FIG. 17). Also, immunoblotting confirmed that the expressed protein binds specifically to the anti-bFGF antibody [M. Seno et al., Hybridoma, 8, 209–221 (1989)] (FIG. 18).

(4) FGF activity of cell extract

From the cells caused to express the mutein as described in (2) above, a cell extract was prepared by the method described in Example 2 (3), followed by determination of FGF activity by the method described in Example 2 (4). The extract from cells of the transformant MM294(DE3)/pLys, pBFM5 was found to possess FGF activity.

The mutein shown in FIG. 16, resulting from replacement of the 69-position Cys and the 87-position Cys by Ser and the 85-position Ser by Cys in human bFGF, was thus obtained.

EXAMPLE 6

Purification of mutein BFM5

(1) Cultivation of producer bacterium

*Escherichia coli* MM294(DE3)/pLysS, pBFM5, which expresses the mutein BFM5, obtained in Example 5, was seeded to 50 ml of an LB medium containing 50 μg/ml ampicillin and 10 μg/ml chloramphenicol and cultivated at 30° C. overnight. This culture broth was added to 1 l of the same medium containing 50 μg/ml ampicillin and 10 μg/ml chloramphenicol and subjected to shaking culture at 30° C. for about 2 hours. When the Klett value reached about 130, isopropyl βD-galactopyranoside (IPTG) was added to reach a final concentration of 0.1 mM. After 3 more hours of cultivation at 30° C., the culture broth was centrifuged at a centrifugal force of about 3000 g for 10 minutes to yield an about 5 g of wet cells.

(2) Purification of mutein

About 5 g of the wet cells obtained in (1) were re-suspended in 30 ml of a buffer containing 20 mM Tris-HCl (pH 7.4), 10% (w/v) sucrose, 10 mM EDTA, 0.2M NaCl and 1 mM phenylmethylsulfonyl fluoride (PMSF) under ice cooling conditions; egg-white lysozyme was added to reach a final concentration of 0.1 mg/ml. After stirring, the mixture was kept standing at 0° C. for 1 hour, followed by addition of dithiothreitol (DTT) to reach a final concentration of 10 mM. While the temperature was kept constant at 0° C., solution viscosity was reduced by sonication, followed by centrifugation at a centrifugal force of about 20,000 g for 40 minutes to yield 30 ml of supernatant. The resulting supernatant was passed through a column (20 ml) of QAE-Toyopearl (Tosoh Corporation), previously equilibrated with 20 mM Tris-HCl (pH 7.4) buffer. The effluent and the solution eluted by column washing with 15 ml of 20 mM Tris-HCl (pH 7.4) buffer were combined. Since gradual precipitation occurred, further centrifugation was performed at a centrifugal force of about 20,000 g for 30 minutes to yield 45 ml of supernatant. This supernatant was passed through a column (40 ml) of CM-Toyopearl (Tosoh Corporation), previously equilibrated with 20 mM Tris-HCl, to adsorb the mutein to the column. After column washing with about 130 ml of a buffer containing 0.1M NaCl, 20 mM Tris-HCl (pH 7.4) and 2 mM DTT, elution was conducted with a buffer containing 1.0M NaCl, 20 mM Tris-HCl (pH 7.4) and 5 mM DTT. The fractions from 15 ml to 45 ml in elution volume were combined, and after adding 30 ml of 20 mM Tris-HCl (pH 7.4) to reduce its salt concentration, the mixture was subjected to heparin affinity chromatography. The column used was Shodex AFpak HR-894 (Showa Denko). This column, previously equilibrated with 20 ml of Tris-HCl (pH 7.4), was washed with 0.5M NaCl and 20 mM Tris-HCl (pH 7.4) after applying the sample, followed by elution on an NaCl density gradient from 0.5M to 2.0M. The mutein was eluted into a single peak at an NaCl concentration of about 1.3M. After the peak fraction was concentrated using an ultrafiltration membrane, it was subjected to gel filtration using Sephadex G-25 (Pharmacia) to replace the buffer with 20 mM sodium citrate (pH 6.5), to yield a purified product. The concentration of the purified product was determined to be 0.941 mg/ml with a yield of 9.88 mg, on the assumption that the molecular extinction coefficient at 280 nm is 13900. This preparation showed a single band (FIG. 19) in polyacrylamide gel electrophoresis using sodium dodecyl sulfate (SDS-PAGE), and had specific activity equivalent to that of bFGF derived from the bovine pituitary gland, as determined by the 3T3 cell growth-promoting activity determination method described in Example 2 (4). Also, this preparation was subjected to amino acid analysis after hydrochloric acid hydrolysis, with performic acid oxidation added before hydrolysis where necessary. As shown in Table 2, the determined amino acid composition agreed substantially with the correct amino acid composition expected from the base sequence shown in FIG. 16.

TABLE 2

Amino acid composition of purified BFM5

| Amino acid | Analytical value | Value expected from FIG. 16 |
| --- | --- | --- |
| Asp | 12 | 12 |
| Thr | 4.5 | 5 |
| Ser | 10.1 | 11 |
| Glu | 12.3 | 12 |
| Pro | 8.8 | 9 |
| Gly | 14.7 | 15 |
| Ala | 8.7 | 9 |
| CysO₃H | 3.1 | 3 |
| Val | 6.6 | 7 |
| Met | 1.9 | 2 |
| Ile | 4.0 | 4 |
| Leu | 13.4 | 13 |
| Tyr | 7.1 | 7 |
| Phe | 8.0 | 8 |
| Lys | 14.2 | 14 |
| His | 3.0 | 3 |
| Arg | 10.9 | 11 |
| Trp | 0.8 | 1 |

TABLE 2-continued

Amino acid composition of purified BFM5

This analysis was conducted after the mutein was hydrolyzed in 6N hydrochloric acid containing 4% thioglycolic acid at 110° C. for 24 hours and 48 hours. Cysteine was quantitated as cysteic acid after performic acid oxidation. The values for serine and threonine were obtained by extrapolating the 0-hour value from the 24- and 48-hour values.

EXAMPLE 7

Purification of mutein BFM4

(1) Cultivation of producer bacterium

The *Escherichia coli* MM294(DE3)/pLysS,pBFM4 obtained in Example 4 was cultivated to express BFM4 in accordance with the method described in Example 6 (1). About 5 g of wet cells were obtained from 1 liter of culture broth by centrifugation.

(2) Purification of mutein

The wet cells obtained in (1) were treated in the same manner as described in Example 6 (2) to finally yield 9.97 mg of purified BFM4. This preparation gave a single band in SDS-PAGE (FIG. 20-A), having a specific activity of 121±28%, relative to bFGF derived from the bovine pituitary gland, as determined by the bioassay described in Example 2 (4).

In FIG. 20-A, lanes 1 through 5 show the results respectively from molecular weight markers (97.4 k, 66.2 k, 45.0 k, 31.0 k, 21.5 k, 14.4 k from above), a QAE-Toyopearl column effluent fraction (4.5 µl), a CM-Toyopearl column eluate (3-fold dilution, 10 µl), a CM-Toyopearl column eluate (3-fold dilution, 3.5 µl), and the purified preparation (1.0 µg).

This preparation was subjected to amino acid analysis after hydrochloric acid hydrolysis. Performic acid oxidation was carried out before hydrolysis to determine Cys content. The results are shown in the column "Before oxidation" in Table 3. As shown in Table 3, this preparation had an amino acid composition agreeing almost completely with the correct amino acid composition expected from the DNA sequence.

EXAMPLE 8

Oxidation of mutein BFM4

The amount of SH groups contained in the purified preparation of mutein BFM4 obtained in Example 7 was determined by the method using 5,5'-dithiobis-(2-nitrobenzoic acid) [J. Sedlak and R. H. Lindsay, Anal. Biochem., 25, 192–205 (1968)]. In the presence of 6M guanidine hydrochloride, 2.8 SH groups per mutein molecule were detected. It was therefore speculated that none of the three cysteine residues in the amino acid sequence had formed an S—S bond. Then, an attempt was made to artificially form an S—S bond using a glutathione redox buffer. In the description below, the molecule wherein all the SH groups in the three cysteine residues are in a reduced state is referred to as reduced BFM4, and the molecule wherein an intramolecular S—S bond has been formed between the 75- and 92-position cysteine residues oxidized BFM4.

Examination revealed that S—S bonds can be efficiently formed by preparing an aqueous solution with the final composition of about 0.3 mg/ml reduced BFM4, 1 mM oxidized glutathione, 0.2 mM reduced glutathione, 1 mM EDTA, 2M urea and 100 mM Tris-HCl (pH 3.0) in an atmosphere containing a minimum amount of air oxygen and keeping it standing at 15° C. for about 24 hours. Because reduced BFM4 and oxidized BFM4 elute separately in reverse phase HPLC, it was easy to analyze the progress of the oxidizing reaction. However, this method could not be used to purify oxidized BFM4 because the BFM4 eluted by reverse phase HPLC had partially lost its activity. The reverse phase HPLC elution patterns of BFM4 obtained before and after oxidation are shown in FIG. 21 (A) and (B). The column used was TSK gel ODS-120T (4.6 mm dia.×250 mm), produced by Tosoh Corporation. The mobile phases used were a 0.1% aqueous solution of trifluoroacetic acid and acetonitrile containing 0.1% trifluoroacetic acid. Elution was conducted while increasing the acetonitrile concentration from 30% to 38% over a period of 16 minutes. The sample was detected by absorbance at 230 nm.

After completion of oxidation, a small amount of citric acid was added to obtain a pH of 6.5, the buffer was replaced with 50 mM sodium citrate (pH 6.5) by gel filtration using Sephadex G-25. Finally, concentration to 0.78 mg/ml was conducted using an ultrafiltration membrane (Diaflo YM5, produced by Amicon Corporation).

The BFM4 thus oxidized was found to contain 1.0 SH group per molecule. Also, in SDS-PAGE under non-reducing conditions, the BFM4 gave almost no band corresponding to the dimer having an intermolecular S—S bond (FIG. 20-B).

In FIG. 20-B, lanes 1 through 3 show the results respectively from molecular weight markers (97.4 k, 66.2 k, 45.0 k, 31.0 k, 21.5 k, 14.4 k from above), BFM4 before oxidation (1.0 μg), and BFM4 after oxidation (1.0 μg).

In the non-reducing SDS-PAGE procedure, electrophoresis was conducted in the same manner as ordinary SDS-PAGE after the sample, mixed with Laemmli's buffer free of 2-mercaptoethanol, was kept standing at room temperature for 10 minutes.

The amino acid composition of the oxidized BFM4 obtained above is shown in the column "After oxidation" in Table 3. As shown in Table 3, the amino acid composition remained unchanged after oxidation; it was thus confirmed that any undesirable modification, such as glutathione addition, had occurred in the oxidized BFM4. Bioassay as described in Example 2 (4) revealed that the specific activity of oxidized BFM4 was 115±13%, relative to bFGF derived from the bovine pituitary gland.

Oxidized BFM4, a bFGF mutein having an intramolecular S—S bond while retaining its activity was thus obtained.

TABLE 3

Amino Acid Composition of BFM4 before and after Oxidation

| Amino acid | Before oxidation | After oxidation | Value expected from the base sequence |
|---|---|---|---|
| Asp | 12 | 12 | 12 |
| Thr | 4.4 | 4.4 | 5 |
| Ser | 10.2 | 10.0 | 12 |
| Glu | 12.3 | 12.3 | 12 |
| Pro | 9.0 | 9.0 | 9 |
| Gly | 14.7 | 14.8 | 15 |
| Ala | 8.0 | 8.0 | 8 |
| CysO$_3$H | 3.6 | 2.9 | 3 |

TABLE 3-continued

Amino Acid Composition of BFM4 before and after Oxidation

| Amino acid | Before oxidation | After oxidation | Value expected from the base sequence |
|---|---|---|---|
| Val | 6.5 | 6.5 | 7 |
| Mat | 2.2 | 2.3 | 2 |
| Ile | 3.7 | 3.7 | 4 |
| Leu | 13.3 | 13.3 | 13 |
| Tyt | 6.8 | 6.7 | 7 |
| Phe | 8.3 | 8.3 | 8 |
| Lys | 13.6 | 13.6 | 14 |
| His | 2.9 | 2.9 | 3 |
| Arg | 10.7 | 10.7 | 11 |
| Trp | 0.8 | 0.5 | 1 |

This amino acid analysis was conducted after the sample was hydrolyzed in 6N hydrochloric acid containing 4% thioglycolic acid at 110° C. for 24 hours. Cysteine was quantified as cysteic acid after performic acid oxidation.

EXAMPLE 9

Stability of oxidized BFM4 to acid

The following experiment was conducted to compare human bFGF (hereinafter referred to as hbFGF), having a wild type sequence, the hbFGF mutein CS23, and oxidized BFM4, with respect to stability under acidic conditions.

Recombinant hbFGF was prepared in accordance with the method described in literature [M. Iwane et al., Biochem. Biophys. Res. Commun., 146, 470–477 (1987)], and used in a 0.57 mg/ml solution in a 50 mM sodium citrate buffer (pH 6.5) containing 1 mM dithiothreitol (DTT). The hbFGF mutein CS23 was prepared in accordance with the method described in literature [M. Seno et al., Biochem. Biophys. Res. Commun., 151, 701–708 (1988)], and used in a 1.00 mg/ml solution in a 50 mM sodium citrate buffer (pH 6.5). The oxidized BFM4 used was prepared as directed in Example 8.

hbFGF, the hbFGF mutein CS23, and oxidized BFM4 were each diluted with acidic buffer A (5 mM Gly-HCl, pH 2.0, 165 mM NaCl) to a final concentration of 10 μg/ml under ice cooling conditions. A 300 μl portion of each solution was transferred to a 1.5 ml polypropylene microtest tube and kept standing at 37° C. After 15, 30, 60 and 120 minutes, a 10 μl sample was taken from each tube and immediately 100 fold diluted with DMEM containing 0.1% BSA (0° C.) to neutralize the acid. After neutralization, each solution was subjected to bioassay as such. Separately, the three proteins were each diluted with DMEM containing 0.1% BSA in place of acidic buffer A; the resulting solution was subjected to bioassay in accordance with the method described in Example 2 (4). The figure obtained in the latter bioassay was taken as 0-minute activity, based on which residual activity in each sample after acid treatment was determined. The results are shown in FIG. 22. In FIG. 22, ▲ denotes the results of oxidized BFM4, ○ denotes the results of hbFGF mutein (S23 and ● denotes the results of hbFGF.

Oxidized BFM4 proved much stabler to acid treatment than hbFGF and still stabler to acid than the hbFGF mutein CS23.

EXAMPLE 10

Stability of oxidized BFM4 to heat

The following experiment was conducted to compare oxidized BFM4, hbFGF and the hbFGF mutein CS23 with respect to thermal stability under neutral pH conditions.

The hbFGF, the hbFGF mutein CS23 and oxidized BFM4 used were the same as used in Example 9. These materials were each diluted with PBS (phosphate buffered saline), pH 7.4, to a final concentration of 10 μl/ml under ice cooling conditions. A 300 μl portion of each solution was transferred to a 1.5 ml polypropylene microtest tube and kept standing at 50° C. After 0, 30, 60, 120 and 180 minutes, a 10 μl sample was taken from each tube and immediately 100 fold diluted with DMEM containing 0.1% BSA (0° C.) and subjected to bioassay. Relative to the activity obtained at 0 minute, taken as 100%, the residual activity in each sample after heat treatment was determined. The results are shown in FIG. 23. In FIG. 23, ▲ denotes the results of oxidized BFM4, ○ denotes the results of hbFGF mutein CS23 and ● denotes the results of hbFGF.

Oxidized BFM4 proved stabler to heat than both of hbFGF and the hbFGF mutein CS23.

The following references, which are referred to for their disclosures at various points in this application, are incorporated herein by reference.

Nature, 249, 123 (1974)
National Cancer Institute Monograph, 48, 109 (1978)
Proc. Natl. Acad. Sci. USA, 82,6507 (1985)
Science, 233, 545 (1986)
Biochem. Biophys. Res. Commun., 135,541 (1986)
EMBO Journal, 5, 2523 (1986)
PCT WO 87/01728
FEBS Letters, 213, 189 (1987)
Biochem. Biophys. Res. Commun., 146,470 (1987)
Science, 251,90 (1991)
Japanese Patent Application Laid-open No. 1-93/1990
EP-A-281,822
Japanese Patent Application Laid-open No. 47198/1991
J. Biochem., 110, 360 (1991)
EP-A-237,966
Biochem. Biophys. Res. Commun., 151,701 (1988)
EP-A-326,907
EP-A-394,951
EP-A-298,728
PCT WO 89/04832
Genetic Engineering, Academic Press (1983), 30–50
Genetic Engineering: Principles and Methods, Plenum Press (1981), 3, 1–32
Gene, 33,103 (1985)
Methods in Enzymology, 101, 20 (1983)
Molecular and General Genetics, 177, 231 (1980)
Methods in Enzymology, 153, 3 (1987)
Gene, 2, 95 (1977)
Gene, 4, 121 (1978)
Gene, 19, 259 (1982)
Gene, 19, 259 (1982)
Biochemical and Biophysical Research Communications, 112, 678 (1983)
Molecular Cloning, Cold Spring Harbor Laboratory, page 239 (1982).
Proceedings of the National Academy of Science, USA, 60, 160 (1968)
Nucleic Acids Research, 9, 309 (1981)
Journal of Molecular Biology, 120, 517 (1978)
Journal of Molecular Biology, 41, 459 (1969)
Genetics, 39, 440 (1954)
Proceedings of the National Academy of Sceince, USA, 73, 4174 (1976)
Japanese Patent Application Laid-open No. 43088/1991.
Gene, 24, 25 (1983)
Journal of Biochemistry, 95, 87 (1984)
Proceedings of the National Academy of Science, USA, 69, 2110 (1972),
Gene, 17, 107 (1982)
Molecular and General General Genetics, 168, 111 (1979)
Proceedings of the National Academy of Science, USA, 75, 1929 (1978)
Virology, 52, 456 (1973)
Journal of Experiments in Molecular Genetics, 431–433, Cold Spring Harbor
Laboratory, New York (1972)
Proceedings of the National Academy of Science, USA, 77, 4505 (1980)
Science, 122, 501 (1952)
Virology, 8, 396 (1959)
Journal of the American Medical Association, 199, 519 (1967)
Proceedings of the Society for the Biological Medicine, 73, 1 (1950)
Biochemistry, 9, 5015 (1970)
Japanese Patent Application Laid-open No. 2-209894/1990)
Journal of Molecular Biology, 189, 113 (1986)
Methods in Enzymology, 195, 60 (1990)
Hybridoma, 8, 209 (1989)
Anal. Biochem. 25, 192 (1968)

|---|---|

What we claim is:

1. A mutein of basic fibroblast qrowth factor (bFGF) wherein at least one amino acid is replaced with a cysteine residue so as to form an intramolecular disulfide bond between
   (a) amino acids 20 and 52,
   (b) amino acids 21 and 142,
   (c) amino acids 27 and 135,
   (d) amino acids 33 and 50,
   (e) amino acids 49 and 69 or
   (f) amino acids 81 and 126,
wherein the amino acid positions refer to the amino acid sequence of FIG. 1 (SEQ ID NO: 11) and wherein scold mutein possesses increased stability under acidic conditions or increased temperature as compared to native bFGF.

2. A mutein of basic fibroblast growth Factor (bFGF) wherein at least one amino acid is replaced with a cysteine residue so as to form an intramolecular disulfide bond between
   (a) amino acids 25 and 118 or
   (b) amino acids 25 and 139,
wherein the amino acid positions refer to the amino acid sequence of FIG. 1 (SEQ ID NO: 11) and wherein said mutein possesses increased stability under acidic conditions or increased temperature as compared to native bFGF.

3. A mutein of basic fibroblast growth factor (bFGF) wherein at least one amino acid is replaced with a cysteine residue so as to form an intramolecular disulfide bond between
   (a) amino acids 75 and 92 or
   (b) amino acids 85 and 92,
wherein the amino acid positions refer to the amino acid sequence of FIG. 1 (SEQ ID NO: 11)and wherein said mutein possesses increased stability under acidic conditions or increased temperature as compared to native bFGF.

4. The mutein according to any one of claims 1, 2, or 3 wherein amino acids 69 and 87 of FIG. 1 (SEQ ID NO: 11) are replaced by a neutral amino acid.

5. The mutein of claim 4 wherein the neutral amino acid is serine.

6. A DNA molecule encoding the mutein according to any one of claims 1, 2, or 3.

7. A vector containing the DNA molecule of claim 6.

8. An isolated transformed cell containing the vector of claim 7.

9. A method of producing the mutein according to any one of claims 1, 2, or 3 comprising culturing in isolated transformed cell having a vector containing a DNA molecule encoding said mutein under conditions suitable for production of said mutein.

10. A pharmaceutical composition comprising the mutein according to any one of claims 1, 2, and 3 and a pharmaceutically acceptable carrier.

11. A method for increasing stability of basic fibroblast growth factor (bFGF) comprising replacing at least one amino acid with a cysteine residue so as to form an intramolecular disulfide bond between
   (a) amino acids 20 and 52,
   (b) amino acids 21 and 142,
   (c) amino acids 27 an 135,
   (d) amino acids 33 and 50,
   (e) amino acids 49 and 69 or
   (f) amino acids 81 and 126,
wherein the amino acid positions refer to the amino acid sequence of FIG. 1 (SEQ ID NO: 11) and wherein the mutated bFGF possesses increased stability under acidic conditions or increased temperature as compared to native bFGF.

12. A method for increasing stability of basic fibroblast growth factor (bFGF) comprising replacing at least one amino acid with a cysteine residue so as to form an intramolecular disulfide bond between
   (a) amino acids 25 and 118 or
   (b) amino acids 25 and 139,
wherein the amino acid positions refer to the amino acid sequence of FIG. 1 (SEQ ID NO: 11)and wherein the mutated bFGF possesses increased stability under acidic conditions or increased temperature as compared to native bFGF.

13. A method for increasing stability of basic fibroblast growth factor (bFGF) comprising replacing at least one amino acid with a cysteine residue so as to form an intramolecular disulfide bond between
   (a) amino acids 75 and 92 or
   (b) amino acids 85 and 92,
wherein the amino acid positions refer to the amino acid sequence of FIG. 1 (SEQ ID NO: 11) and wherein the mutated bFGF possesses increased stability under acidic conditions or increased temperature as compared to native bFGF.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: YES ( x i ) SEQUENCE DESCRIPTION: SEQ ID NO:1:

CAGTTCGTTT GCATGCCACA TAC    23

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Synthetic DNA (iii) HYPOTHETICAL: NO (iv) ANTI-SENSE: YES (xi) SEQUENCE DESCRIPTION: SEQ ID NO:2:

CATTGGAAGA CAAAGTATAG C    21

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Synthetic DNA (iii) HYPOTHETICAL: NO (iv) ANTI-SENSE: YES (xi) SEQUENCE DESCRIPTION: SEQ ID NO:3:

TTCCTTCATA CACAGGTAAC GA    22

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Synthetic DNA (iii) HYPOTHETICAL: NO (iv) ANTI-SENSE: YES (xi) SEQUENCE DESCRIPTION: SEQ ID NO:4:

AACAGACTTG CATGCTAGTA ATCT    24

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Synthetic DNA (iii) HYPOTHETICAL: NO (iv) ANTI-SENSE: YES (xi) SEQUENCE DESCRIPTION: SEQ ID NO:5:

TGCTGGCATA TGATTCGTAA TC    22

(2) INFORMATION FOR SEQ ID NO:6:

( i ) SEQUENCE CHARACTERISTICS:
    ( A ) LENGTH: 444 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( A ) ORGANISM: HUMAN ( i x ) FEATURE:
    ( A ) NAME/KEY: CDS
    ( B ) LOCATION: 4..441

( x i ) SEQUENCE DESCRIPTION: SEQ ID NO:6:

| ATG | CCA | GCA | TTG | CCC | GAG | GAT | GGC | GGC | AGC | GGC | GCC | TTC | CCG | CCC | GGC | 48 |
|---|---|---|---|---|---|---|---|---|---|---|---|---|---|---|---|---|
|  | Pro | Ala | Leu | Pro | Glu | Asp | Gly | Gly | Ser | Gly | Ala | Phe | Pro | Pro | Gly |  |
|  | 1 |  |  |  | 5 |  |  |  |  | 10 |  |  |  |  | 15 |  |
| CAC | TTC | AAG | GAC | CCC | AAG | CGG | CTG | TAC | TGC | AAA | AAC | GGG | GGC | TTC | TTC | 96 |
| His | Phe | Lys | Asp | Pro | Lys | Arg | Leu | Tyr | Cys | Lys | Asn | Gly | Gly | Phe | Phe |  |
|  |  |  |  | 20 |  |  |  |  | 25 |  |  |  |  | 30 |  |  |
| CTG | CGC | ATC | CAC | CCC | GAC | GGC | CGA | GTT | GAC | GGG | GTC | CGG | GAG | AAG | AGC | 144 |
| Leu | Arg | Ile | His | Pro | Asp | Gly | Arg | Val | Asp | Gly | Val | Arg | Glu | Lys | Ser |  |
|  |  |  | 35 |  |  |  |  | 40 |  |  |  |  | 45 |  |  |  |
| GAC | CCT | CAC | ATC | AAG | CTA | CAA | CTT | CAA | GCA | GAA | GAG | AGA | GGA | GTT | GTG | 192 |
| Asp | Pro | His | Ile | Lys | Leu | Gln | Leu | Gln | Ala | Glu | Glu | Arg | Gly | Val | Val |  |
|  |  | 50 |  |  |  |  | 55 |  |  |  |  | 60 |  |  |  |  |
| TCT | ATC | AAA | GGA | GTG | TGT | GCT | AAC | CGT | TAC | CTG | GCT | ATG | AAG | GAA | GAT | 240 |
| Ser | Ile | Lys | Gly | Val | Cys | Ala | Asn | Arg | Tyr | Leu | Ala | Met | Lys | Glu | Asp |  |
|  | 65 |  |  |  |  | 70 |  |  |  |  | 75 |  |  |  |  |  |
| GGA | AGA | TTA | CTG | GCT | TCT | AAA | TGT | GTT | ACG | GAT | GAG | TGT | TTC | TTT | TTT | 288 |
| Gly | Arg | Leu | Leu | Ala | Ser | Lys | Cys | Val | Thr | Asp | Glu | Cys | Phe | Phe | Phe |  |
| 80 |  |  |  |  | 85 |  |  |  |  | 90 |  |  |  |  | 95 |  |
| GAA | CGA | TTG | GAA | TCT | AAT | AAC | TAC | AAT | ACT | TAC | CGG | TCA | AGG | AAA | TAC | 336 |
| Glu | Arg | Leu | Glu | Ser | Asn | Asn | Tyr | Asn | Thr | Tyr | Arg | Ser | Arg | Lys | Tyr |  |
|  |  |  |  | 100 |  |  |  |  | 105 |  |  |  |  | 110 |  |  |
| ACC | AGT | TGG | TAT | GTG | GCA | CTG | AAA | CGA | ACT | GGG | CAG | TAT | AAA | CTT | GGA | 384 |
| Thr | Ser | Trp | Tyr | Val | Ala | Leu | Lys | Arg | Thr | Gly | Gln | Tyr | Lys | Leu | Gly |  |
|  |  |  | 115 |  |  |  |  | 120 |  |  |  |  | 125 |  |  |  |
| TCC | AAA | ACA | GGA | CCT | GGG | CAG | AAA | GCT | ATA | CTT | TTT | CTT | CCA | ATG | TCT | 432 |
| Ser | Lys | Thr | Gly | Pro | Gly | Gln | Lys | Ala | Ile | Leu | Phe | Leu | Pro | Met | Ser |  |
|  |  | 130 |  |  |  |  | 135 |  |  |  |  | 140 |  |  |  |  |
| GCT | AAG | AGC | TGA |  |  |  |  |  |  |  |  |  |  |  |  | 444 |
| Ala | Lys | Ser |  |  |  |  |  |  |  |  |  |  |  |  |  |  |
|  | 145 |  |  |  |  |  |  |  |  |  |  |  |  |  |  |  |

( 2 ) INFORMATION FOR SEQ ID NO:7:

( i ) SEQUENCE CHARACTERISTICS:
    ( A ) LENGTH: 444 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
    ( A ) NAME/KEY: CDS
    ( B ) LOCATION: 4..441

( x i ) SEQUENCE DESCRIPTION: SEQ ID NO:7:

```
ATG CCA GCA TTG CCC GAG GAT GGC GGC AGC GGC GCC TTC CCG CCC GGC        48
    Pro Ala Leu Pro Glu Asp Gly Gly Ser Gly Ala Phe Pro Pro Gly
    1               5                   10                  15

CAC TTC AAG GAC CCC AAG CGG CTG TAC TGC AAA AAC GGG GGC TTC TTC        96
His Phe Lys Asp Pro Lys Arg Leu Tyr Cys Lys Asn Gly Gly Phe Phe
                20                  25                  30

CTG CGC ATC CAC CCC GAC GGC CGA GTT GAC GGG GTC CGG GAG AAG AGC       144
Leu Arg Ile His Pro Asp Gly Arg Val Asp Gly Val Arg Glu Lys Ser
            35                  40                  45

GAC CCT CAC ATC AAG CTA CAA CTT CAA GCA GAA GAG AGA GGA GTT GTG       192
Asp Pro His Ile Lys Leu Gln Leu Gln Ala Glu Glu Arg Gly Val Val
        50                  55                  60

TCT ATC AAA GGA GTG AGC GCT AAT CGT TAC CTG GCT ATG AAG GAA GAT       240
Ser Ile Lys Gly Val Ser Ala Asn Arg Tyr Leu Ala Met Lys Glu Asp
    65                  70                  75

GGA AGA TTA CTA GCT TCT AAG TCT GTT ACG GAT GAG TGT TTC TTT TTT       288
Gly Arg Leu Leu Ala Ser Lys Ser Val Thr Asp Glu Cys Phe Phe Phe
80                  85                  90                  95

GAA CGA TTG GAA TCT AAT AAC TAC AAT ACT TAC CGG TCA AGG AAA TAC       336
Glu Arg Leu Glu Ser Asn Asn Tyr Asn Thr Tyr Arg Ser Arg Lys Tyr
                100                 105                 110

ACC AGT TGG TAT GTG GCA TGC AAA CGA ACT GGG CAG TAT AAA CTT GGA       384
Thr Ser Trp Tyr Val Ala Cys Lys Arg Thr Gly Gln Tyr Lys Leu Gly
            115                 120                 125

TCC AAA ACA GGA CCT GGG CAG AAA GCT ATA CTT TTT CTT CCA ATG TCT       432
Ser Lys Thr Gly Pro Gly Gln Lys Ala Ile Leu Phe Leu Pro Met Ser
        130                 135                 140

GCT AAG AGC TGA                                                       444
Ala Lys Ser
    145
```

( 2 ) INFORMATION FOR SEQ ID NO:8:

( i ) SEQUENCE CHARACTERISTICS:
        ( A ) LENGTH: 444 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 4..441

( x i ) SEQUENCE DESCRIPTION: SEQ ID NO:8:

```
ATG CCA GCA TTG CCC GAG GAT GGC GGC AGC GGC GCC TTC CCG CCC GGC        48
    Pro Ala Leu Pro Glu Asp Gly Gly Ser Gly Ala Phe Pro Pro Gly
    1               5                   10                  15

CAC TTC AAG GAC CCC AAG CGG CTG TAC TGC AAA AAC GGG GGC TTC TTC        96
His Phe Lys Asp Pro Lys Arg Leu Tyr Cys Lys Asn Gly Gly Phe Phe
                20                  25                  30

CTG CGC ATC CAC CCC GAC GGC CGA GTT GAC GGG GTC CGG GAG AAG AGC       144
Leu Arg Ile His Pro Asp Gly Arg Val Asp Gly Val Arg Glu Lys Ser
            35                  40                  45

GAC CCT CAC ATC AAG CTA CAA CTT CAA GCA GAA GAG AGA GGA GTT GTG       192
Asp Pro His Ile Lys Leu Gln Leu Gln Ala Glu Glu Arg Gly Val Val
        50                  55                  60
```

| | | | | | | | | | | | | | | | | |
|---|---|---|---|---|---|---|---|---|---|---|---|---|---|---|---|---|
| TCT | ATC | AAA | GGA | GTG | AGC | GCT | AAT | CGT | TAC | CTG | GCT | ATG | AAG | GAA | GAT | 240 |
| Ser | Ile | Lys | Gly | Val | Ser | Ala | Asn | Arg | Tyr | Leu | Ala | Met | Lys | Glu | Asp | |
| | 65 | | | | 70 | | | | | 75 | | | | | | |
| GGA | AGA | TTA | CTA | GCT | TCT | AAG | TCT | GTT | ACG | GAT | GAG | TGT | TTC | TTT | TTT | 288 |
| Gly | Arg | Leu | Leu | Ala | Ser | Lys | Ser | Val | Thr | Asp | Glu | Cys | Phe | Phe | Phe | |
| 80 | | | | | 85 | | | | | 90 | | | | | 95 | |
| GAA | CGA | TTG | GAA | TCT | AAT | AAC | TAC | AAT | ACT | TAC | CGG | TCA | AGG | AAA | TAC | 336 |
| Glu | Arg | Leu | Glu | Ser | Asn | Asn | Tyr | Asn | Thr | Tyr | Arg | Ser | Arg | Lys | Tyr | |
| | | | | 100 | | | | | 105 | | | | | 110 | | |
| ACC | AGT | TGG | TAT | GTG | GCA | CTG | AAA | CGA | ACT | GGG | CAG | TAT | AAA | CTT | GGA | 384 |
| Thr | Ser | Trp | Tyr | Val | Ala | Leu | Lys | Arg | Thr | Gly | Gln | Tyr | Lys | Leu | Gly | |
| | | | 115 | | | | | 120 | | | | | 125 | | | |
| TCC | AAA | ACA | GGA | CCT | GGG | CAG | AAA | GCT | ATA | CTT | TGT | CTT | CCA | ATG | TCT | 432 |
| Ser | Lys | Thr | Gly | Pro | Gly | Gln | Lys | Ala | Ile | Leu | Cys | Leu | Pro | Met | Ser | |
| | | 130 | | | | | 135 | | | | | 140 | | | | |
| GCT | AAG | AGC | TGA | | | | | | | | | | | | | 444 |
| Ala | Lys | Ser | | | | | | | | | | | | | | |
| | | 145 | | | | | | | | | | | | | | |

(2) INFORMATION FOR SEQ ID NO:9:

(i) SEQUENCE CHARACTERISTICS:
        (A) LENGTH: 444 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 4..441

(xi) SEQUENCE DESCRIPTION: SEQ ID NO:9:

| | | | | | | | | | | | | | | | | |
|---|---|---|---|---|---|---|---|---|---|---|---|---|---|---|---|---|
| ATG | CCA | GCA | TTG | CCC | GAG | GAT | GGC | GGC | AGC | GGC | GCC | TTC | CCG | CCC | GGC | 48 |
| | Pro | Ala | Leu | Pro | Glu | Asp | Gly | Gly | Ser | Gly | Ala | Phe | Pro | Pro | Gly | |
| | 1 | | | | 5 | | | | | 10 | | | | | 15 | |
| CAC | TTC | AAG | GAC | CCC | AAG | CGG | CTG | TAC | TGC | AAA | AAC | GGG | GGC | TTC | TTC | 96 |
| His | Phe | Lys | Asp | Pro | Lys | Arg | Leu | Tyr | Cys | Lys | Asn | Gly | Gly | Phe | Phe | |
| | | | 20 | | | | | 25 | | | | | 30 | | | |
| CTG | CGC | ATC | CAC | CCC | GAC | GGC | CGA | GTT | GAC | GGG | GTC | CGG | GAG | AAG | AGC | 144 |
| Leu | Arg | Ile | His | Pro | Asp | Gly | Arg | Val | Asp | Gly | Val | Arg | Glu | Lys | Ser | |
| | | | 35 | | | | | 40 | | | | | 45 | | | |
| GAC | CCT | CAC | ATC | AAG | CTA | CAA | CTT | CAA | GCA | GAA | GAG | AGA | GGA | GTT | GTG | 192 |
| Asp | Pro | His | Ile | Lys | Leu | Gln | Leu | Gln | Ala | Glu | Glu | Arg | Gly | Val | Val | |
| | | 50 | | | | | 55 | | | | | 60 | | | | |
| TCT | ATC | AAA | GGA | GTG | AGC | GCT | AAT | CGT | TAC | CTG | TGT | ATG | AAG | GAA | GAT | 240 |
| Ser | Ile | Lys | Gly | Val | Ser | Ala | Asn | Arg | Tyr | Leu | Cys | Met | Lys | Glu | Asp | |
| | 65 | | | | 70 | | | | | 75 | | | | | | |
| GGA | AGA | TTA | CTA | GCT | TCT | AAG | TCT | GTT | ACG | GAT | GAG | TGT | TTC | TTT | TTT | 288 |
| Gly | Arg | Leu | Leu | Ala | Ser | Lys | Ser | Val | Thr | Asp | Glu | Cys | Phe | Phe | Phe | |
| 80 | | | | | 85 | | | | | 90 | | | | | 95 | |
| GAA | CGA | TTG | GAA | TCT | AAT | AAC | TAC | AAT | ACT | TAC | CGG | TCA | AGG | AAA | TAC | 336 |
| Glu | Arg | Leu | Glu | Ser | Asn | Asn | Tyr | Asn | Thr | Tyr | Arg | Ser | Arg | Lys | Tyr | |
| | | | | 100 | | | | | 105 | | | | | 110 | | |
| ACC | AGT | TGG | TAT | GTG | GCA | CTG | AAA | CGA | ACT | GGG | CAG | TAT | AAA | CTT | GGA | 384 |
| Thr | Ser | Trp | Tyr | Val | Ala | Leu | Lys | Arg | Thr | Gly | Gln | Tyr | Lys | Leu | Gly | |
| | | | 115 | | | | | 120 | | | | | 125 | | | |
| TCC | AAA | ACA | GGA | CCT | GGG | CAG | AAA | GCT | ATA | CTT | TTT | CTT | CCA | ATG | TCT | 432 |
| Ser | Lys | Thr | Gly | Pro | Gly | Gln | Lys | Ala | Ile | Leu | Phe | Leu | Pro | Met | Ser | |
| | | 130 | | | | | 135 | | | | | 140 | | | | |

```
GCT  AAG  AGC  TGA                                                                                        444
Ala  Lys  Ser
     145
```

( 2 ) INFORMATION FOR SEQ ID NO:10:

( i ) SEQUENCE CHARACTERISTICS:
        ( A ) LENGTH: 444 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 4..441

( x i ) SEQUENCE DESCRIPTION: SEQ ID NO:10:

```
ATG  CCA  GCA  TTG  CCC  GAG  GAT  GGC  GGC  AGC  GGC  GCC  TTC  CCG  CCC  GGC           48
     Pro  Ala  Leu  Pro  Glu  Asp  Gly  Gly  Ser  Gly  Ala  Phe  Pro  Pro  Gly
       1              5                        10                       15

CAC  TTC  AAG  GAC  CCC  AAG  CGG  CTG  TAC  TGC  AAA  AAC  GGG  GGC  TTC  TTC           96
His  Phe  Lys  Asp  Pro  Lys  Arg  Leu  Tyr  Cys  Lys  Asn  Gly  Gly  Phe  Phe
                    20                       25                       30

CTG  CGC  ATC  CAC  CCC  GAC  GGC  CGA  GTT  GAC  GGG  GTC  CGG  GAG  AAG  AGC          144
Leu  Arg  Ile  His  Pro  Asp  Gly  Arg  Val  Asp  Gly  Val  Arg  Glu  Lys  Ser
               35                       40                       45

GAC  CCT  CAC  ATC  AAG  CTA  CAA  CTT  CAA  GCA  GAA  GAG  AGA  GGA  GTT  GTG          192
Asp  Pro  His  Ile  Lys  Leu  Gln  Leu  Gln  Ala  Glu  Glu  Arg  Gly  Val  Val
          50                       55                       60

TCT  ATC  AAA  GGA  GTG  AGC  GCT  AAT  CGT  TAC  CTG  GCT  ATG  AAG  GAA  GAT          240
Ser  Ile  Lys  Gly  Val  Ser  Ala  Asn  Arg  Tyr  Leu  Ala  Met  Lys  Glu  Asp
     65                       70                       75

GGA  AGA  TTA  CTA  GCA  TGC  AAG  TCT  GTT  ACG  GAT  GAG  TGT  TTC  TTT  TTT          288
Gly  Arg  Leu  Leu  Ala  Cys  Lys  Ser  Val  Thr  Asp  Glu  Cys  Phe  Phe  Phe
 80                      85                       90                       95

GAA  CGA  TTG  GAA  TCT  AAT  AAC  TAC  AAT  ACT  TAC  CGG  TCA  AGG  AAA  TAC          336
Glu  Arg  Leu  Glu  Ser  Asn  Asn  Tyr  Asn  Thr  Tyr  Arg  Ser  Arg  Lys  Tyr
                    100                      105                      110

ACC  AGT  TGG  TAT  GTG  GCA  CTG  AAA  CGA  ACT  GGG  CAG  TAT  AAA  CTT  GGA          384
Thr  Ser  Trp  Tyr  Val  Ala  Leu  Lys  Arg  Thr  Gly  Gln  Tyr  Lys  Leu  Gly
               115                      120                      125

TCC  AAA  ACA  GGA  CCT  GGG  CAG  AAA  GCT  ATA  CTT  TTT  CTT  CCA  ATG  TCT          432
Ser  Lys  Thr  Gly  Pro  Gly  Gln  Lys  Ala  Ile  Leu  Phe  Leu  Pro  Met  Ser
          130                      135                      140

GCT  AAG  AGC  TGA                                                                        444
Ala  Lys  Ser
     145
```

( 2 ) INFORMATION FOR SEQ ID NO:11:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:11:

| Pro | Ala | Leu | Pro | Glu | Asp | Gly | Gly | Ser | Gly | Ala | Phe | Pro | Pro | Gly | His |
|---|---|---|---|---|---|---|---|---|---|---|---|---|---|---|---|
| 1 | | | | 5 | | | | | 10 | | | | | 15 | |

| Phe | Lys | Asp | Pro | Lys | Arg | Leu | Tyr | Cys | Lys | Asn | Gly | Gly | Phe | Phe | Leu |
|---|---|---|---|---|---|---|---|---|---|---|---|---|---|---|---|
| | | | 20 | | | | | 25 | | | | | 30 | | |

| Arg | Ile | His | Pro | Asp | Gly | Arg | Val | Asp | Gly | Val | Arg | Glu | Lys | Ser | Asp |
|---|---|---|---|---|---|---|---|---|---|---|---|---|---|---|---|
| | | 35 | | | | | 40 | | | | | 45 | | | |

| Pro | His | Ile | Lys | Leu | Gln | Leu | Gln | Ala | Glu | Glu | Arg | Gly | Val | Val | Ser |
|---|---|---|---|---|---|---|---|---|---|---|---|---|---|---|---|
| | 50 | | | | | 55 | | | | | 60 | | | | |

| Ile | Lys | Gly | Val | Cys | Ala | Asn | Arg | Tyr | Leu | Ala | Met | Lys | Glu | Asp | Gly |
|---|---|---|---|---|---|---|---|---|---|---|---|---|---|---|---|
| 65 | | | | | 70 | | | | | 75 | | | | | 80 |

| Arg | Leu | Leu | Ala | Ser | Lys | Cys | Val | Thr | Asp | Glu | Cys | Phe | Phe | Phe | Glu |
|---|---|---|---|---|---|---|---|---|---|---|---|---|---|---|---|
| | | | | 85 | | | | | 90 | | | | | 95 | |

| Arg | Leu | Glu | Ser | Asn | Asn | Tyr | Asn | Thr | Tyr | Arg | Ser | Arg | Lys | Tyr | Thr |
|---|---|---|---|---|---|---|---|---|---|---|---|---|---|---|---|
| | | | 100 | | | | | 105 | | | | | 110 | | |

| Ser | Trp | Tyr | Val | Ala | Leu | Lys | Arg | Thr | Gly | Gln | Tyr | Lys | Leu | Gly | Ser |
|---|---|---|---|---|---|---|---|---|---|---|---|---|---|---|---|
| | | 115 | | | | | 120 | | | | | 125 | | | |

| Lys | Thr | Gly | Pro | Gly | Gln | Lys | Ala | Ile | Leu | Phe | Leu | Pro | Met | Ser | Ala |
|---|---|---|---|---|---|---|---|---|---|---|---|---|---|---|---|
| | 130 | | | | | 135 | | | | | 140 | | | | |

| Lys | Ser |
|---|---|
| 145 | |

( 2 ) INFORMATION FOR SEQ ID NO:12:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:12:

| Pro | Ala | Leu | Pro | Glu | Asp | Gly | Gly | Ser | Gly | Ala | Phe | Pro | Pro | Gly | His |
|---|---|---|---|---|---|---|---|---|---|---|---|---|---|---|---|
| 1 | | | | 5 | | | | | 10 | | | | | 15 | |

| Phe | Lys | Asp | Pro | Lys | Arg | Leu | Tyr | Cys | Lys | Asn | Gly | Gly | Phe | Phe | Leu |
|---|---|---|---|---|---|---|---|---|---|---|---|---|---|---|---|
| | | | 20 | | | | | 25 | | | | | 30 | | |

| Arg | Ile | His | Pro | Asp | Gly | Arg | Val | Asp | Gly | Val | Arg | Glu | Lys | Ser | Asp |
|---|---|---|---|---|---|---|---|---|---|---|---|---|---|---|---|
| | | 35 | | | | | 40 | | | | | 45 | | | |

| Pro | His | Ile | Lys | Leu | Gln | Leu | Gln | Ala | Glu | Glu | Arg | Gly | Val | Val | Ser |
|---|---|---|---|---|---|---|---|---|---|---|---|---|---|---|---|
| | 50 | | | | | 55 | | | | | 60 | | | | |

| Ile | Lys | Gly | Val | Ser | Ala | Asn | Arg | Tyr | Leu | Ala | Met | Lys | Glu | Asp | Gly |
|---|---|---|---|---|---|---|---|---|---|---|---|---|---|---|---|
| 65 | | | | | 70 | | | | | 75 | | | | | 80 |

| Arg | Leu | Leu | Ala | Ser | Lys | Ser | Val | Thr | Asp | Glu | Cys | Phe | Phe | Phe | Glu |
|---|---|---|---|---|---|---|---|---|---|---|---|---|---|---|---|
| | | | | 85 | | | | | 90 | | | | | 95 | |

| Arg | Leu | Glu | Ser | Asn | Asn | Tyr | Asn | Thr | Tyr | Arg | Ser | Arg | Lys | Tyr | Thr |
|---|---|---|---|---|---|---|---|---|---|---|---|---|---|---|---|
| | | | 100 | | | | | 105 | | | | | 110 | | |

| Ser | Trp | Tyr | Val | Ala | Cys | Lys | Arg | Thr | Gly | Gln | Tyr | Lys | Leu | Gly | Ser |
|---|---|---|---|---|---|---|---|---|---|---|---|---|---|---|---|

|  |  |  |  |  | 115 |  |  |  |  | 120 |  |  |  |  | 125 |  |  |  |  |
|---|---|---|---|---|---|---|---|---|---|---|---|---|---|---|---|---|---|---|---|---|

Lys Thr Gly Pro Gly Gln Lys Ala Ile Leu Phe Leu Pro Met Ser Ala
    130                     135                 140

Lys Ser
145

(2) INFORMATION FOR SEQ ID NO:13:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:13:

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Ser Ala Asn Arg Tyr Leu Ala Met Lys Glu Asp Gly
65                  70                  75                  80

Arg Leu Leu Ala Ser Lys Ser Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Cys Leu Pro Met Ser Ala
    130                     135                 140

Lys Ser
145

(2) INFORMATION FOR SEQ ID NO:14:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

| Pro | Ala | Leu | Pro | Glu | Asp | Gly | Gly | Ser | Gly | Ala | Phe | Pro | Pro | Gly | His |
|---|---|---|---|---|---|---|---|---|---|---|---|---|---|---|---|
| 1 | | | | 5 | | | | | 10 | | | | | | 15 |

| Phe | Lys | Asp | Pro | Lys | Arg | Leu | Tyr | Cys | Lys | Asn | Gly | Gly | Phe | Phe | Leu |
|---|---|---|---|---|---|---|---|---|---|---|---|---|---|---|---|
| | | | 20 | | | | | 25 | | | | | 30 | | |

| Arg | Ile | His | Pro | Asp | Gly | Arg | Val | Asp | Gly | Val | Arg | Glu | Lys | Ser | Asp |
|---|---|---|---|---|---|---|---|---|---|---|---|---|---|---|---|
| | | 35 | | | | | 40 | | | | | 45 | | | |

| Pro | His | Ile | Lys | Leu | Gln | Leu | Gln | Ala | Glu | Glu | Arg | Gly | Val | Val | Ser |
|---|---|---|---|---|---|---|---|---|---|---|---|---|---|---|---|
| | 50 | | | | | 55 | | | | | 60 | | | | |

| Ile | Lys | Gly | Val | Ser | Ala | Asn | Arg | Tyr | Leu | Cys | Met | Lys | Glu | Asp | Gly |
|---|---|---|---|---|---|---|---|---|---|---|---|---|---|---|---|
| 65 | | | | | 70 | | | | | 75 | | | | | 80 |

| Arg | Leu | Leu | Ala | Ser | Lys | Ser | Val | Thr | Asp | Glu | Cys | Phe | Phe | Phe | Glu |
|---|---|---|---|---|---|---|---|---|---|---|---|---|---|---|---|
| | | | | 85 | | | | | 90 | | | | | 95 | |

| Arg | Leu | Glu | Ser | Asn | Asn | Tyr | Asn | Thr | Tyr | Arg | Ser | Arg | Lys | Tyr | Thr |
|---|---|---|---|---|---|---|---|---|---|---|---|---|---|---|---|
| | | | 100 | | | | | 105 | | | | | 110 | | |

| Ser | Trp | Tyr | Val | Ala | Leu | Lys | Arg | Thr | Gly | Gln | Tyr | Lys | Leu | Gly | Ser |
|---|---|---|---|---|---|---|---|---|---|---|---|---|---|---|---|
| | | 115 | | | | | 120 | | | | | 125 | | | |

| Lys | Thr | Gly | Pro | Gly | Gln | Lys | Ala | Ile | Leu | Phe | Leu | Pro | Met | Ser | Ala |
|---|---|---|---|---|---|---|---|---|---|---|---|---|---|---|---|
| | 130 | | | | | 135 | | | | | 140 | | | | |

| Lys | Ser |
|---|---|
| 145 | |

( 2 ) INFORMATION FOR SEQ ID NO:15:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:15:

| Pro | Ala | Leu | Pro | Glu | Asp | Gly | Gly | Ser | Gly | Ala | Phe | Pro | Pro | Gly | His |
|---|---|---|---|---|---|---|---|---|---|---|---|---|---|---|---|
| 1 | | | | 5 | | | | | 10 | | | | | | 15 |

| Phe | Lys | Asp | Pro | Lys | Arg | Leu | Tyr | Cys | Lys | Asn | Gly | Gly | Phe | Phe | Leu |
|---|---|---|---|---|---|---|---|---|---|---|---|---|---|---|---|
| | | | 20 | | | | | 25 | | | | | 30 | | |

| Arg | Ile | His | Pro | Asp | Gly | Arg | Val | Asp | Gly | Val | Arg | Glu | Lys | Ser | Asp |
|---|---|---|---|---|---|---|---|---|---|---|---|---|---|---|---|
| | | 35 | | | | | 40 | | | | | 45 | | | |

| Pro | His | Ile | Lys | Leu | Gln | Leu | Gln | Ala | Glu | Glu | Arg | Gly | Val | Val | Ser |
|---|---|---|---|---|---|---|---|---|---|---|---|---|---|---|---|
| | 50 | | | | | 55 | | | | | 60 | | | | |

| Ile | Lys | Gly | Val | Ser | Ala | Asn | Arg | Tyr | Leu | Ala | Met | Lys | Glu | Asp | Gly |
|---|---|---|---|---|---|---|---|---|---|---|---|---|---|---|---|
| 65 | | | | | 70 | | | | | 75 | | | | | 80 |

| Arg | Leu | Leu | Ala | Cys | Lys | Ser | Val | Thr | Asp | Glu | Cys | Phe | Phe | Phe | Glu |
|---|---|---|---|---|---|---|---|---|---|---|---|---|---|---|---|
| | | | | 85 | | | | | 90 | | | | | 95 | |

| Arg | Leu | Glu | Ser | Asn | Asn | Tyr | Asn | Thr | Tyr | Arg | Ser | Arg | Lys | Tyr | Thr |
|---|---|---|---|---|---|---|---|---|---|---|---|---|---|---|---|
| | | | 100 | | | | | 105 | | | | | 110 | | |

| Ser | Trp | Tyr | Val | Ala | Leu | Lys | Arg | Thr | Gly | Gln | Tyr | Lys | Leu | Gly | Ser |
|---|---|---|---|---|---|---|---|---|---|---|---|---|---|---|---|
| | | 115 | | | | | 120 | | | | | 125 | | | |

| Lys | Thr | Gly | Pro | Gly | Gln | Lys | Ala | Ile | Leu | Phe | Leu | Pro | Met | Ser | Ala |
|---|---|---|---|---|---|---|---|---|---|---|---|---|---|---|---|
| | 130 | | | | | 135 | | | | | 140 | | | | |

| Lys | Ser |